(12) United States Patent
Fladby et al.

(10) Patent No.: US 9,625,474 B2
(45) Date of Patent: Apr. 18, 2017

(54) DIAGNOSTIC METHOD FOR ALZHEIMER'S DISEASE

(75) Inventors: Tormod Fladby, Lorenskog (NO); Lisbeth Johnsen, Lorenskog (NO); Kaj Blennow, Molndal (SE)

(73) Assignee: INVEN2 AS, Oslo (NO)

( * ) Notice: Subject to any disclaimer, the term of this patent is extended or adjusted under 35 U.S.C. 154(b) by 82 days.

(21) Appl. No.: 12/867,479

(22) PCT Filed: Feb. 13, 2009

(86) PCT No.: PCT/EP2009/001210
§ 371 (c)(1),
(2), (4) Date: Jan. 14, 2011

(87) PCT Pub. No.: WO2009/100953
PCT Pub. Date: Aug. 20, 2009

(65) Prior Publication Data
US 2011/0124010 A1 May 26, 2011

(30) Foreign Application Priority Data
Feb. 15, 2008 (GB) .................................. 0802851.6

(51) Int. Cl.
*G01N 33/68* (2006.01)
*G01N 33/569* (2006.01)

(52) U.S. Cl.
CPC ... *G01N 33/6893* (2013.01); *G01N 33/56972* (2013.01); *G01N 33/6848* (2013.01); *G01N 2333/70596* (2013.01); *G01N 2800/2821* (2013.01)

(58) Field of Classification Search
None
See application file for complete search history.

(56) References Cited

U.S. PATENT DOCUMENTS

2007/0202554 A1  8/2007  Hamaoki

FOREIGN PATENT DOCUMENTS

WO  WO 97/33175        9/1997
WO  WO 2010/034072 A1  4/2010

OTHER PUBLICATIONS

Holland et al., Rapid Commun in Mass Spect, 10:1227-1232, 1997.*
Fiala et al., Eur J of Clin Invest., 32:360-371, 2002.*
Majumbar et al., Neurobiol of Aging, 29:707-715, Jan. 2007.*
Zaghi et al., Acta Neuropathol., 117:111-124, 2009.*
Mattsson et al., Neuromol Med., 13:151-159, 2011.*
Fabriek et al., Journal of Neuroimmunology, 161:190-194, 2005.*
Weller, J Neuropathol and Exp Neurol., 57(10):885-894, Oct. 1998.*
Green et al., Neuroscience Letters 259:133-135, 1999.*
Leroy et al., Nature, 395:451-452, 1998.*
Kim et al., The FASEB Journal, 18(13):1615-1617, Epublished Aug. 2, 2004.*
Jung et al., Neurobiology of Aging, 20:249-257, 1999.*
Uljon et al., Protein and Peptide Analysis: New Mass Spectrometric Applications, From: Methods in Molecular Biology, vol. 146, Edited by: J. R. Chapman, Humana Press Inc., Totowa, NJ, (2000).*
Jongen et al., J Neurol, Neurosurg, and Psychiatry, 63:446-451, 1997.*
Guseo A., Eur Neurol, 15:169-176, 1977.*
Fiala et al., Ineffective phagocytosis of amyloid-beta by macrophages of Alzheimer's disease patients, J Alzheimers Dis 7(3):221-232, 2005.*
Ziegler-Heitbrock L., The CD14+ CD16+ blood monocytes: their role in infection and inflammation, J. Leukoc. Biol. 81: 584-592; 2007.*
Paresce et al., Slow degradation of aggregates of the Alzheimer's disease amyloid beta-protein by microglial cells, J Biol Chem, 272:29390-29397, 1997.*
Ziegler-Heitbrock, Immunology Today, 17(9):424-428, Sep. 1996.*
Lee et al., Int J Biochem & Cell Biol, 40(9):1835-1849, Epub Jan. 20, 2008.*
National Institute on Aging, Preventing Alzheimer's Disease: What Do We Know?, Sep. 2012. Retreived online from <https://www.nia.nih.gov/alzheimers/publication/preventing-alzheimers-disease/introduction> Retrieved on Aug. 23, 2016.*
Avagyan et al., "Immune Blood Biomarkers of Alzheimer Disease Patients," *Journ. of Neuroimmunology*, vol. 210, pp. 67-72 (2009).
Buddenhagen et al., "Phagocytic Activity of CSF Monocytes in Neurological Diseases," *Journal of Neurology*, vol. 234, No. 4, pp. 257-258 (1987).
DeKosky et al., "Alzheimer Research Forum Live Discussion: Memantine: Implicants for Treating Alzheimer's," *Journ. of Alzheimer's Disease*, pp. 255-262 (2005).
Dos Reis-Filho et al., "Semiologic Value of Erythrocyte Macrophages in the Cerebrospinal Fluid," *Arquivos De Neuro-Psiquiatria*, vol. 38, No. 3, pp. 231-236 (1980). [English Abstract at p. 235].
Fiala et al., "Ineffective Phagocytosis of Amyloidβ by Macrophages of Alzheimer's Disease Patients," *Journal of Alzheimer's Disease*, vol. 7, pp. 221-232 (2005).

(Continued)

*Primary Examiner* — Kimberly A. Ballard
*Assistant Examiner* — Stacey N MacFarlane
(74) *Attorney, Agent, or Firm* — Foley & Lardner LLP

(57) ABSTRACT

A method of detecting the presence, or monitoring the severity of a condition characterized by the presence of fragments of a marker protein in the brain of a patient. The method comprises: (i) providing a sample comprising macrophages obtained from the patient; and (ii) detecting the presence of the marker protein or fragments thereof in the macrophages. The presence of abnormal levels of the marker protein and/or fragments thereof in the macrophages is indicative of the presence of the condition in the patient. The condition and the marker proteins can be: Alzheimer's Disease and the Abeta peptide, Parkinson's Disease and ubiquitin, Multiple Sclerosis and myelin basic protein, FrontoTemporal Dementia and tau, Amyotrophic Lateral Sclerosis and tau, Parkinson's disease, Lewy Body dementia or Alzheimer's Disease and alpha-synuclein.

9 Claims, 15 Drawing Sheets

(56) References Cited

OTHER PUBLICATIONS

Hasegawa et al., "NF-kB Activation in Peripheral Blood Mononuclear Cells in Neonatal Asphyxia," *Clinical and Experimental Immunology*, vol. 132, No. 2, pp. 261-264 (2003).
Jung et al., "β-Amyloid Precursor Protein is Detectable on Monocytes and is Increased in Alzheimer's Disease," *Neurobiology of Aging*, vol. 20, No. 3, pp, 249-257 (1999).
Kim et al., "Microglia, Major Player in the Brain Inflammation: Their roles in the Pathogenesis of Parkinson's Disease," *Experimental & Molecular Medicine*, vol. 38, No. 4, pp. 333-347 (2006).
Liu et al., "LPS Receptor (CD14): A Receptor for Phagocytosis of Alzheimer's Amyloid Peptide," *Brain*, vol. 128, pp. 1778-1789 (2005).
Maier et al., "Distinct Fractional Aβ Release Patterns in Human Mononuclear Phagocytes," *Journal of Neuroimmunology*, vol. 206, pp. 1-4 (2009).
Morgan et al., "Dynamic Complexity of the Microglial Activation Response in Transgenic Models of Amyloid Deposition: Implications for Alzheimer Therapeutics," *J. Neuropathol Exp. Neurol.*, vol. 64, No. 9, pp. 743-753 (2005).
Oe et al., "Quantitative Analysis of Amyloid β Peptides in Cerebrospinal Fluid of Alzheimer's Disease Patients by Immunoaffinity Purification and Stable Isotope Dilution Liquid Chromatography/Negative Electrospray Ionization Tandem Mass Spectrometry," *Rapid Communications in Mass Spectrometry*, vol. 20, No. 24, pp. 3723-3735 (2006).
Oide et al., "Regression Stage Senile Plaques in the Natural Course of Alzheimer's Disease," *Neuropathology and Applied Neuropathology*, vol. 32, No. 5, pp. 539-556 (2006).
Schenk, "Amyloid-beta immunotherapy for Alzheimer's disease: the end of the beginning," *Nat. Rev. Neuroscience*, vol. 3, No. 10 pp. 824-828 (2002).
Schenk, et al., "Immunization with amyloid-beta attenuates Alzheimer-disease-like pathology in the PDAPP mouse," *Nature*, vol. 400, pp. 173-177 (1999).
Simard, et al., "Bone marrow-derived microglia play a critical role in restricting senile plaque formation in Alzheimer's disease," *Neuron*, vol. 49, No. 4, pp. 489-502 (2006).
Vehmas et al., "Immune Reactive Cells in Senile Plaques and Cognitive Decline in Alzeimer's Disease," *Neurobiology of Aging*, vol. 24, No. 2, pp. 321-331 (2003).
Wetterberg et al., "Micrometer-sized Particles in Cerebrospinal Fluid (CSF) in Patients with Schizophrenia," *Neurosci. Lett.*, vol. 329, pp. 91-95 (2002).
Wilcock et al., "Passive Amyloid Immunotherapy Clears Amyloid and Transiently Activates Microglia in a Transgenic Mouse Model of Amyloid Deposition," *The Journal of Neuroscience*, vol. 24, No. 27, pp. 6144-6151 (2004).
Zhang et al., "Aggregated α-Synuclein Activates Microglia: A Process Leading to Disease Progression in Parkinson's Disease," *The FASEB Journ.*, vol. 19, pp. 533-542 (2005).
Austin et al., "Amyloid Precursor Protein Mediates a Tyrosine Kinase-Dependent Activation Response in Endothelial Cells", The Journal of Neuroscience: the Official Journal for the Society for Neuroscience, vol. 29, Issue 46, 2009, 12 pages.
Bissel et al., "Systemic and Brain Macrophage Infections in Relation to the Development of Simian Immunodeficiency Virus Encephalitis", Journal of Virology, American Society for Microbiology, vol. 82, Issue 10, 2008, pp. 5031-5042.
Chang et al., Monocyte to Macophage Differentiation: Synthesis and Secretion of a Complex Extracellular Matrix, The Journal of Biological Chemistry, vol. 287, No. 17, Feb. 20, 2012, pp. 14122-14135.
Fischer-Smith et al., "Monocyte/Macrophage Trafficking in Acquired Immunodeficiency Syndrome Encephalitis: Lessons from Human and Nonhuman Primate Studies", Journal of Neurovirology, Stockton Press, vol. 14, Part 4, 2008, pp. 318-326.
Gannon et al., "Current Understanding of HIV-associated Neurocognitive Disorders Pathogenesis", Current Opinion in Neurology, vol. 24, Issue 3, 2011, pp. 275-283.
Kapoor et al., "Cerebrospinal Fluid Outflow: An Evolving Perspective", Brain Research Bulletin, Elsevier Science B.V. Amsterdam, vol. 77, Issue 6, 2008, pp. 327-344.
Koh et al., "Integration of the Subarachnoid Space and Lymphatics; Is it Time to Embrace a New Concept of Cerebrospinal Fluid Absorption?", Cerebrospinal Fluid Research, 2:6, Sep. 20, 2005, 11 pages.
Laspuir et al., "CSF Proteomic Fingerprints for HIV-associated Cognitive Impairment", Journal of Neuroimmunology, Elsevier Science B.V. Amsterdam, vol. 192, Issue 1-2, 2007, pp. 157-170.
Levine et al., "Systems Analysis of Human Brain Gene Expression: Mechanisms for HIV-Associated Neurocognitive Impairment and Common Pathways with Alzheimer's Disease", BMC Medical Genomics, 6:4, 2013, 20 pages.
Magaki et al., "Immunophenotypes in the Circulation of Patients with Mild Cognitive Impairment", Journal of Psychiatric Research, Elsevier Science B.V. Amsterdam, vol. 42, Issue 3, 2008, pp. 240-246.
Pulliam, Lynn, "HIV Regulation of Amyloid Beta Production", Journal of Neuroimmune Pharmacology, 4:213-217, 2009, 5 pages.
Sondag et al., "Adhesion of Monocytes to Type I Collagen Stimulates an APP-Dependent Proinflamatory signaling response and release of Aβ 1-40", Journal of Neuroinflammation, 7:22, 2010, 11 pages.
Scott et al., "Inability to Detect β-Amyloid Protein Precursor mRNA in Alzheimer Plaque-Associated Microglia," Experimental Neurology, vol. 121, pp. 113-118, 1993.
Sierra et al., "Janus-faced microglia: beneficial and detrimental consequences of microglial phagocytosis," Frontiers in Cellular Neurosciences, vol. 7, Article 6, pp. 1-22, Jan. 2013.
Itoh et al., "Expression of amyloid precursor protein after rat traumatic brain injury," Neurological Research, vol. 31, pp. 103-109, Feb. 2009.
Storey et al., "Amyloid precursor protein of Alzheimer's disease: evidence for a stable, full-length, trans-membrane pool in primary neuronal cultures," European Journal of Neuroscience, vol. 11, pp. 1779-1788, 1999.
ABCAM®, "Anti-Amyloid Precursor Protein antibody," Product Datasheet, http://www.abcam.cn/Amyloid-Precursor-Protein-antibody-3G12-ab49449.html, accessed Feb. 18, 2014.
Thermo Fischer Scientific, "Amyloid beta Antibody (2C8)," www.thermocom/pierce, accessed Feb. 18, 2014.
Covance, "Beta Amyloid, 1-16 (6E10) Monoclonal Antibody," Product Information Sheet, https://store.crpinc.com/datasheet.aspx?catalogno=sig-39300, accessed Feb. 14, 2014.
Roberts et al.,"Induction of Pathogenic Sets of Genes in Macrophages and Neurons in NeuroAIDS," vol. 162, No. 6, pp. 2041-2057, Jun. 2003.
Lan et al., "HIV-1 reduces Aβ-Degrading Enzymatic Activities in Primary Human Monomuclear Phagocytes," J. Immunol., vol. 186, pp. 6925-6932, May 6, 2011.
Ziegler-Heitbrock, "Heterogeneity of human blood monocytes: the CD14+ and CD16+ subpopulation," Immunology Today, vol. 17, No. 9, pp. 424-428, Sep. 1996.
Butler et al., "Potential Compensatory Responses Through Autophagic/Lysosomal Pathways in Neurodegenerative Diseases," Autophagy, vol. 2, No. 3, pp. 234-237, Jul.-Sep. 2006.
Burster et al., "Differential Processing of Autoantigens in Lysosomes from Human Monocyte-Derived and Peripheral Blood Dendritic Cells," The Journal of Immunology, vol. 175, No. 9, pp. 5940-5949, Nov. 2005.
EXPASY Bioinformatics Resource Portal, "Peptide Cutter," http://web.expasy.org/peptide_cutter, accessed Nov. 6, 2015.

* cited by examiner

SEQUENCE LISTING

<160> NUMBER OF SEQ ID NOS: 5

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile

```
                20                  25                  30

Gly Leu Met Val Gly Val Val Ile Ala
            35                  40

<210> SEQ ID NO 2
<211> LENGTH: 76
<212> TYPE: PRT
<213> ORGANISM: Homo sapiens

<400> SEQUENCE: 2

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 3
<211> LENGTH: 304
<212> TYPE: PRT
<213> ORGANISM: Homo sapiens

<400> SEQUENCE: 3

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
            85                  90                  95

Arg Asp Ala Pro Gly Arg Glu Asp Asn Thr Phe Lys Asp Arg Pro Ser
        100                 105                 110

Glu Ser Asp Glu Leu Gln Thr Ile Gln Glu Asp Ser Ala Ala Thr Ser
    115                 120                 125

Glu Ser Leu Asp Val Met Ala Ser Gln Lys Arg Pro Ser Gln Arg His
130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
            165                 170                 175

Arg Phe Phe Gly Gly Asp Arg Gly Ala Pro Lys Arg Gly Ser Gly Lys
        180                 185                 190

Asp Ser His His Pro Ala Arg Thr Ala His Tyr Gly Ser Leu Pro Gln
    195                 200                 205

Lys Ser His Gly Arg Thr Gln Asp Glu Asn Pro Val Val His Phe Phe
210                 215                 220

Lys Asn Ile Val Thr Pro Arg Thr Pro Pro Pro Ser Gln Gly Lys Gly
```

```
            225                 230                 235                 240
Arg Gly Leu Ser Leu Ser Arg Phe Ser Trp Gly Ala Glu Gly Gln Arg
                    245                 250                 255

Pro Gly Phe Gly Tyr Gly Gly Arg Ala Ser Asp Tyr Lys Ser Ala His
                260                 265                 270

Lys Gly Phe Lys Gly Val Asp Ala Gln Gly Thr Leu Ser Lys Ile Phe
                275                 280                 285

Lys Leu Gly Gly Arg Asp Ser Arg Ser Gly Ser Pro Met Ala Arg Arg
290                 295                 300

<210> SEQ ID NO 4
<211> LENGTH: 758
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
                100                 105                 110

Ser Leu Glu Asp Glu Ala Ala Gly His Val Thr Gln Glu Pro Glu Ser
            115                 120                 125

Gly Lys Val Val Gln Glu Gly Phe Leu Arg Glu Pro Gly Pro Pro Gly
        130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300
```

-continued

```
Val Glu Ile Thr Pro Asn Val Gln Lys Glu Gln Ala His Ser Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
```

```
                    725                 730                 735
Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 5
<211> LENGTH: 140
<212> TYPE: PRT
<213> ORGANISM: Homo sapiens

<400> SEQUENCE: 5

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

DIAGNOSTIC METHOD FOR ALZHEIMER'S DISEASE

FIELD OF THE INVENTION

The present invention relates to a method of detecting the presence of or monitoring the severity of a condition characterised by the presence of fragments of a marker protein in the brain of a patient.

BACKGROUND

Alzheimer's disease (AD) is by far the most frequent disease causing dementia, and AD-like mechanisms like amyloid deposition are also implicated in the two next most common causes, vascular (VaD) and dementia with Lewy bodies (DLB). AD runs a protracted course from the time of diagnosis and is detrimental also to the health of caregivers [1, 2]. In a system of managed care, AD also is a severe burden to the public health system [3], the economic impact is by some estimates already larger than that of cancer, stroke and heart disease [4, 5]. AD prevalence increases from 10% above 65 years of age, to 50% among those above 85 [6, 7] and may quadruple by 2050 due to incidence rates that increase exponentially with age [8] and a larger number of elderly [9].

Today, we appear to be on the verge of therapy against Alzheimer's disease (AD) progression [10]. This will dramatically increase the importance of precise early diagnosis, and will shift the research focus towards an understanding of the process of AD disease induction.

The characterization of patients with Mild Cognitive Impairment (MCI) [11] and recent proposed research criteria for AD [12] help identify a patient group with increased risk for progressive dementia [13]. It is known that AD initiation and progression is linked to central nervous system (CNS) APP (amyloid precursor protein) production; the metabolism of APP to A$\beta$42 protein by $\beta$- and $\gamma$-secretase; and the deposition of the A$\beta$42 protein in amyloid plaques [14, 15]. Tau aggregation, microtubule disassembly and neurofibrillary degeneration follows [10, 16, 17], possibly as a result of interaction with A$\beta$42 [18-20]. Disease development is strongly influenced by genetic disposition [21, 22], but probably also by epigenetic and acquired risk factors like cerebrovascular disease [23] and proteomic [24] and immunological [25] mechanisms. The concentration of A$\beta$42 in cerebro-spinal fluid (CSF) reflects CNS parenchymal levels and increases with age above 50 [26]. However, the concentration of A$\beta$42 in CSF is reduced in patients that develop AD [27, 28] probably due to the deposition in amyloid plaques [29].

The length of the time span from AD initiation to development of dementia in individual patients is unknown. Evidence from autopsies performed on patients that have died of unrelated causes suggests that limited early stage AD-like damage may occur decades earlier [30], but the natural evolution of these lesions is unknown. An extended preclinical phase from disease initiation to clinical dementia may give a large therapeutic time-window.

Dementia is preceded by mild cognitive impairment (MCI) [11, 13, 31]. At this stage, some patients are at increased risk of progression to dementia (annual rate of conversion of 6-25%, [13]), though others may have a condition limited to MCI for a number of years. Imaging evidence indicates that a subgroup of patients with MCI has brain amyloid deposition [32-34]. This evidence supports results from studies with CFS markers, where low levels of the amyloid precursor CSF A$\beta$42 linked to cerebral amyloid deposition [18, 29] tend to be found in MCI subgroups that subsequently progress to Alzheimer dementia. Many of these patients satisfy new AD research criteria [12]. As described above, neuropsychology, CSF proteomics and neuroimaging have contributed to increased understanding of MCI. Induction of disease occurs earlier, and a period of latency may overlap with the MCI stage, as the disease becomes detectable.

However, there is still no reliable means for detecting the early stages of AD, even though these early periods may turn out to be clinically valuable for implementation of disease modifying therapies [35]. This is significant because, at later stages, the widespread damage caused by AD is most likely irreversible [16]. Therefore, early detection of AD is important to its effective treatment.

Fiala M. et al. [39] reports on a study in which monocytes (CD68 positive cells) obtained from blood samples of AD patients and control individuals were differentiated into macrophages and then exposed to A$\beta$ protein in vitro. The A$\beta$ protein was conjugated with a visible marker and the cells examined by fluorescence or confocal microscopy in order to determine uptake of A$\beta$ protein. The study indicates that the macrophages derived from AD patients were inefficient in A$\beta$ protein phagocytosis compared with the control. However, the approach taken in this study is rather laborious and it is not clear at what stage in the development of AD this technique would provide a positive result.

Other pathological conditions of the central nervous system which are characterised by the presence of fragments of a marker protein the brain include Parkinson's Disease, Multiple Sclerosis, Fronto Temporal Dementia and Amyotrophic Lateral Sclerosis. In each case, early diagnosis of the condition is desirable.

Therefore, the present invention seeks to alleviate one or more of the above problems and provide an improved method of detecting the presence or monitoring the severity of a condition, characterised by the presence of fragments of a marker protein in the brain of a patient.

SUMMARY OF THE INVENTION

According to one aspect of the present invention, there is provided a method of detecting the presence, or monitoring the severity, of a condition characterised by the presence of fragments of a marker in the brain of a patient comprising the steps of:

(i) providing a sample obtained from the patient, wherein the sample comprises activated macrophages; and (ii) detecting the presence of the marker protein or fragments thereof in the macrophages, wherein abnormal levels of the marker protein and/or fragments thereof in the macrophages are indicative of the presence or severity of the condition in the patient.

It is preferred that: the condition is Alzheimer's Disease and the marker protein is the A$\beta$ peptide; the condition is Parkinson's Disease and the marker protein is ubiquitin; the condition is Multiple Sclerosis and the marker protein is myelin basic protein; the condition is FrontoTemporal Dementia and the marker protein is the tau protein; or the condition is Amyotrophic Lateral Sclerosis and the marker protein is the tau protein; or the condition is Parkinson's Disease, Lewy body dementia or Alzheimer's Disease and the marker protein is alpha-synuclein.

Conveniently, the sample is a cerebro-spinal fluid sample or a blood sample.

Preferably, step (ii) comprises detecting the presence of the marker protein or fragments thereof that were present in the patient.

Advantageously, the presence of abnormal levels of the marker protein and/or fragments thereof is a reduction in the levels, an increase in the levels, or the absence, of the marker protein and/or fragments thereof. In particular, where the condition is Alzheimer's Disease, Parkinson's Disease, FrontoTemporal Dementia, Amyotrophic Lateral Sclerosis or Lewy body dementia, the marker protein levels are reduced or absent. Where the condition is Multiple Sclerosis, the marker protein levels are increased.

Alternatively, the presence of abnormal levels of the marker protein and/or fragments thereof is the presence of an abnormal pattern of marker protein fragments.

Conveniently, step (ii) comprises comparing the levels of the marker protein and/or fragments thereof in the macrophages in the sample with the levels of the marker protein and/or fragments thereof in macrophages obtained from cerebro-spinal fluid from an individual without the condition.

Alternatively, step (ii) comprises comparing the levels of the marker protein and/or fragments thereof with a standard level, the standard level being an average of the levels of the marker protein and/or fragments thereof in macrophages obtained from cerebrospinal fluid from a plurality of individuals without the condition, wherein the level of the marker protein and/or fragments thereof is abnormal if there is a statistically significant difference from the standard level.

Preferably said macrophages display the CD14 and/or CD16 cell surface markers.

Advantageously, step (i) further comprises the step of sorting a plurality of cells obtained from the patient and selecting the activated macrophages in order to provide the sample.

Conveniently, the step of sorting comprises using fluorescence activated cell sorting or magnetic extraction.

Preferably, step (ii) comprises lysing the macrophages and immunoprecipitating the marker protein and/or fragments thereof.

Advantageously, step (ii) comprises detecting the marker protein and/or fragments thereof using mass spectrometry, preferably matrix-assisted laser desorption/ionisation time of flight mass spectrometry.

Alternatively, step (ii) comprises detecting the marker protein and/or fragments thereof using HPLC-fluorescence, HPLC-UV, luminescence or streptavidin/biotin systems.

Conveniently, step (ii) comprises: contacting the marker protein with a target antibody capable of binding the marker protein; contacting the target antibody with a secondary antibody capable of binding the target antibody or the marker protein; and detecting the presence of the secondary antibody.

Preferably, the secondary antibody comprises a detectable label and step ii) comprises detecting the detactable label.

Advantageously, the detectable label is a nucleic acid marker and step (ii) comprises detecting the nucleic acid marker using a nucleic acid amplification reaction.

Conveniently, the method further comprises the step of detecting at least one additional marker of the condition, wherein the presence of said additional marker and the presence of abnormal levels of the marker protein and/or fragments thereof in the macrophages or microglia is indicative of the presence of the condition in the patient.

Preferably, the condition is Alzheimer's Disease and said at least one additional maker of Alzheimer's Disease is abnormal levels of Aβ42, Tau, Phospho-Tau, Abeta42/Abeta40 ratio, or combinations thereof, in a sample of cerebro-spinal fluid obtained from the patient, or in an RNA profile in blood or CSF obtained from the patient.

Advantageously, the abnormal levels of the additional marker in a sample of CSF obtained from the patient are: a Aβ42 protein concentration of less than 550 pg/ml; a Phospho-Tau concentration of greater than 85 pg/ml; or ([Aβ42]/[Aβ40])×10 is less than 1.

Conveniently, the condition is Alzheimer's Disease and the marker protein is the Aβ peptide and wherein the Aβ peptide comprises a sequence having a sequence identity of at least 70%, preferably at least 80%, more preferably at least 90%, more preferably at least 95%, more preferably at least 99%, most preferably at least 100% to SEQ. ID NO. 1.

Alternatively, the condition is Parkinson's Disease and the marker protein is ubiquitin and wherein the ubiquitin protein sequence comprises a sequence having a sequence identity of at least 70%, preferably at least 80%, more preferably at least 90%, more preferably at least 95%, more preferably at least 99%, most preferably at least 100% to SEQ. ID NO. 2.

Alternatively, the condition is Multiple Sclerosis and the marker protein is the myelin basic protein and wherein the myelin basic protein sequence comprises a sequence having a sequence identity of at least 70%, preferably at least 80%, more preferably at least 90%, more preferably at least 95%, more preferably at least 99%, most preferably at least 100% to SEQ. ID NO. 3.

Alternatively, the condition is FrontoTemporal Dementia or Amyotrophic Lateral Sclerosis and the marker protein is tau protein and wherein the tau protein sequence comprises a sequence having a sequence identity of at least 70%, preferably at least 80%, more preferably at least 90%, more preferably at least 95%, more preferably at least 99%, most preferably at least 100% to SEQ. ID NO. 4.

Alternatively, the condition is Parkinson's Disease, Lewy body dementia or Alzheimer's Disease and the marker protein is alpha-synuclein protein and wherein the alpha-synuclein protein sequence comprises a sequence having a sequence identity of at least 70%, preferably at least 80%, more preferably at least 90%, more preferably at least 95%, more preferably at least 99%, most preferably at least 100% to SEQ. ID NO. 5.

According to another aspect of the present invention, there is provided a kit suitable for detecting the presence of, or monitoring the severity of, a condition characterised by the presence of fragments of a marker protein in the brain of a patient, wherein the kit comprises:
 a target-specific binding reagent capable of binding the marker protein; and
 a macrophage-specific binding reagent capable of specifically binding a macrophage.

Conveniently, the kit further comprises a secondary binding reagent capable of binding the target specific binding reagent or the marker protein, wherein the secondary binding reagent is coupled to a label.

Preferably, the label is a nucleic acid marker molecule.

Advantageously, one, both or all of the target specific binding reagent, the macrophage specific binding reagent and optionally the secondary binding reagent are antibodies or antigen binding fragments thereof.

Conveniently, the macrophage specific binding reagent is bound to a magnetic bead.

Preferably, the kit further comprises a cell lysing agent.

Advantageously, the macrophage specific binding reagent is capable of binding the CD14 or CD16 cell markers.

Conveniently, the kit comprises a plurality of target specific binding reagents, each capable of binding a different marker protein.

Preferably, the or each marker protein is selected from a group consisting of the α-beta protein, ubiquitin, myelin basic protein, the tau protein and the α-synuclein protein.

According to a further aspect of the present invention, there is provided the use of a kit of the invention in detecting the presence of, or monitoring the severity, a condition characterised by the presence of fragments of a marker protein in the brain of a patient, from a sample obtained from a patient.

This invention relates to a strategy of diagnosing and monitoring diseases in the central nervous system (CNS). The approach of the present invention studies the immune cells, such as macrophages/microglia, in samples of, for example, cerebrospinal fluid (CSF) and blood, and measures abnormal levels or the absence of intracellular disease-specific peptides or proteins. Activation of the macrophage/microglia system and phagocytosis of disease specific peptides/proteins provides a novel diagnostic tool and enables the progress and efficacy of therapeutic interventions to be assessed.

While not wishing to be bound by theory, it is believed that the invention operates due to the molecular and physiological mechanisms that will now be described in relation to the specific example of Alzheimer's Disease. It is believed that the natural evolution of Alzheimer pathology involves an extended preclinical period. The role of the immune system is extremely interesting in this connection. It is known that immunization of an individual with Aβ peptides triggers phagocytosis [36], and that this may ameliorate amyloid deposition in transgenic AD-mice (possibly also human AD, but a clinical trial was terminated after patients developed encephalomyelitis [37]). Immune activity may also be involved in the natural evolution of amyloid pathology, i.e. the continuous level of phagocytic activity may contribute to plaque load over time. Supporting this, there is evidence that macrophages circulate from the bone marrow to the CNS in pathological conditions and contribute to plaque clearing in AD mice [38]. There is also evidence for reduced phagocytosis of Aβ by macrophages of AD patients in vitro [39]. Therefore, it is believed that the present invention operates by measuring the lack of phagocytic activity of macrophages and/or microglia in vivo and uses this for diagnostic purposes.

Embodiments of the present invention utilise IP-MS (immuno-precipitation mass spectrometry) to enable monitoring of macrophage/monocyte phagocytic activity in vivo. This opens new territory for the monitoring of Aβ phagocytosis in patients predisposed to AD either genetically or with subjective memory failure.

The same principle may also be used to study other disease groups. The detection in macrophages of a specific biomarker protein (other than Aβ peptides) which is involved in the mechanism of another disease is used for the early diagnosis and monitoring of the other disease. Some specific examples will now be described.

1. The progress of Multiple Sclerosis (MS) involves loss of myelin sheet insulating axons. Immune activation and phagocytosis are involved in the demyelination process. An important disease specific marker is therefore myelin basic protein (MBP).
2. In Parkinson's Disease, ubiquitin is found accumulated in disease specific inclusion bodies called Lewy bodies. Ubiquitin is a highly conserved small regulatory protein involved in the control of stability, function, and intracellular localization of a wide variety of proteins. The identification of abnormal accumulations of the ubiquitin protein inside cells that are markers of Parkinson's Disease is therefore envisaged in one embodiment of the present invention.
3. Alpha-synuclein is a protein found primarily in neural tissue, where it is seen mainly in presynaptic terminals. The protein can aggregate to form insoluble fibrils in pathological conditions characterized by Lewy bodies, such as Parkinson and Lewy body dementia. A fragmented variant of alpha-synuclein is also found in amyloid plaques in Alzheimer's Disease.
4. Tau proteins are microtubule-associated proteins that are abundant in neurons where the main function is to modulate the stability of axonal microtubules. Various tau aggregates are also involved in diseases such as Amyotrophic Lateral Sclerosis (ALS), AD, Parkinson and fronto temporal dementias.

The examples mentioned above illustrate important disease specific protein markers (1-4) that are known to accumulate (2-4) in neurodegenerative diseases. Therefore, in order to effect early diagnosis and monitoring of the progress of these diseases, the same general approach as is described herein in relation to Alzheimer's Disease is taken, except that an alternative panel of antibodies (which are specific for the protein characterising the disease, and fragments of the protein) is used to withdraw the protein of interest in the immuno-precipitation step.

It is to be appreciated that in the conditions listed in 2-4, above, a marker protein is phagocytosed at abnormally low levels by macrophages and thus abnormally low levels of the marker protein in macrophages from an individual are indicative of the condition. With regard to Multiple Sclerosis the MBP marker protein is believed to be phagocytosed by macrophages at abnormally high levels and thus the detection of abnormally high levels of the marker protein is indicative of Multiple Sclerosis in the patient.

In this specification, the term "monitoring the presence or measuring the severity" of a condition includes diagnosing the condition but also includes the assessment of the progress of the condition after initial diagnosis, monitoring the response of the condition to a treatment; and establishing the extent of a patient's condition (i.e. staging).

In this specification, the term "macrophage" includes the term "microglia". Typically, the term "macrophage" is used when the cell is in the CSF and the term "microglia" is used when the cell is in the CNS.

In this specification, the percentage "identity" between two sequences is determined using the BLASTP algorithm version 2.2.2 (Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402) using default parameters. In particular, the BLAST algorithm can be accessed on the internet using the URL http://www.ncbi.nlm.nih.gov/blast/.

BRIEF DESCRIPTION OF DRAWINGS

FIG. 10 shows confocal microscopy images of a macrophage from CSF stained for intracellular MBP, where

FIG. 11 shows confocal microscopy images of a macrophage from CSF stained with isotype-specific antibodies, where

FIG. 12 shows confocal microscopy images of a macrophage from blood stained with intracellular MBP, where

FIG. 13 shows confocal microscopy images of a macrophage from blood stained with isotype-specific antibody, where

FIG. 14 shows confocal microscopy images of a macrophage from blood with no primary antibody against intracellular antigens, where

BRIEF DESCRIPTION OF THE SEQUENCES

Figure 1:
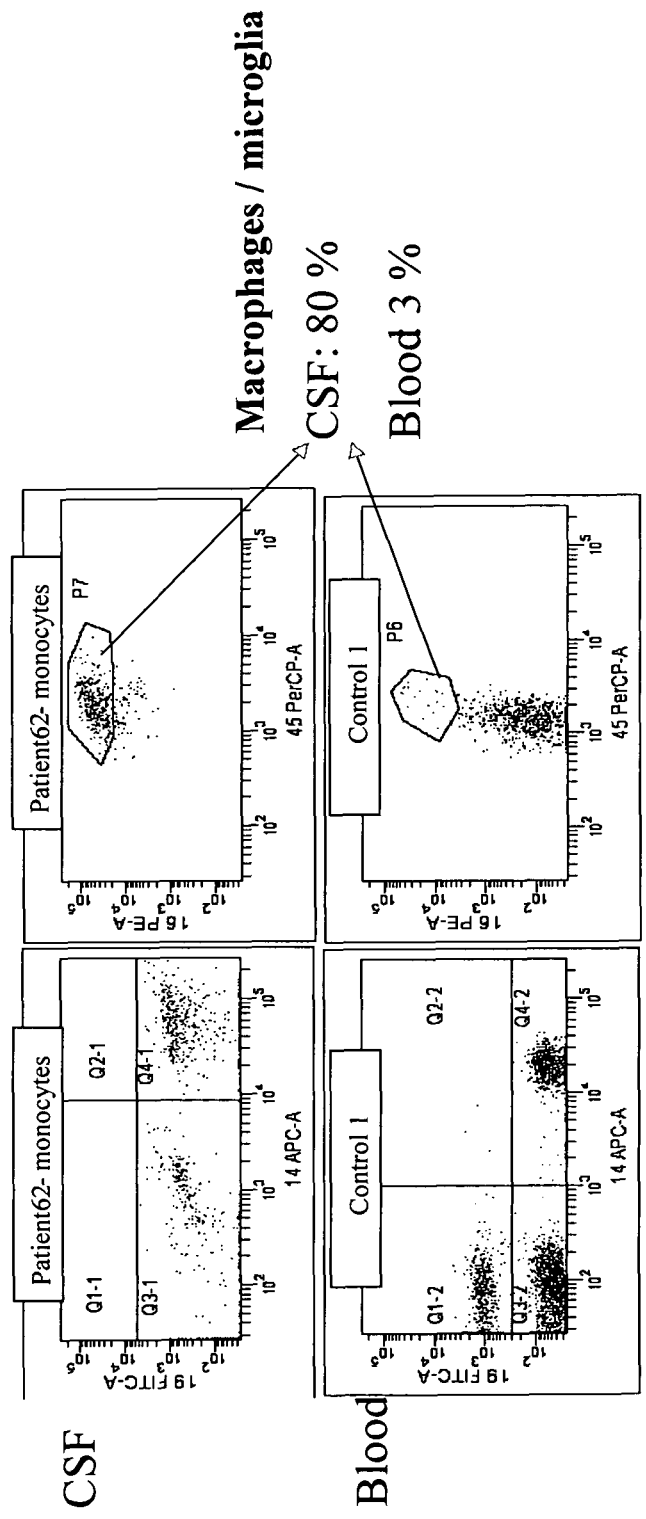
FIG. 1 is a flowplot of monocytes from the CSF of a patient diagnosed with non-AD/MCI (top panel) and a corresponding flowplot from a blood donor (bottom panel). The encircled cell population is activated macrophages/microglia.

SEQ. ID NO.: 1 is the amino acid sequence of the Aβ protein.

SEQ. ID NO.: 2 is the amino acid sequence of the Ubiquitin protein (RPS27A)

SEQ. ID NO.: 3 is the amino acid sequence of the Myelin basic protein (MBP).

SEQ. ID NO.: 4 is the amino acid sequence of the Tau protein (MAPT).

SEQ. ID NO.: 5 is the amino acid sequence of the alpha-synuclein protein (SNCA).

DETAILED DESCRIPTION

In embodiments of the present invention, the peptide/protein content of activated macrophages is used for the early diagnosis of AD as will now be explained. The data disclosed herein (see, for example, FIGS. 3 to 5) indicate that macrophages in AD have a reduced capacity for Aβ phagocytosis. Most of the patients studied as reported herein are patients with AD according to Dubois et al. [12], with MCI but not dementia. This suggests that reduced phagocytosis may be present early in disease development.

An embodiment of the present invention will now be described. A sample of cerebrospinal fluid (CSF) is obtained from a patient by lumbar puncture. The macrophages in the sample are stained with fluorescent-labelled anti-CD14 and anti-CD16 antibodies and the macrophages are then withdrawn from the sample by fluorescence activated cell sorting.

The cells are selected on the basis of CD14 and CD16 expression because this enables activated macrophages to be differentiated from quiescent cells (increasing CD16 expression signifies an activated status). This technique also avoids the inadvertent sampling of other cell types such as CD68 positive dendritic cells. This approach contrasts with that reported by Fiala et al (39) in which CD68 positive cells were selected.

The resultant macrophage cells are lysed and prepared for protein analysis. The cell lysate is mixed with monoclonal antibodies capable of binding fragments of the Aβ protein (SEQ. ID NO.: 1). Exemplary antibodies are 6E10, 4G8 and 11A50-B10 from Signet Laboratories, Inc. The 6E10 antibody is used to immunoprecipitate Aβ fragments 1-16, the 4G8 antibody immunoprecipitates Aβ fragments 17-24 and the 11A50-B10 antibody immunoprecipitates Aβ fragments of 1-40. In alternative embodiments, a different panel of antibodies, specific for other fragments, may be used. The monoclonal antibodies are also coupled to magnetic beads, for example, with beads bound to anti-IgG antibodies. The magnetic beads are used to extract the fragments of the Aβ protein. The antibodies and beads are subsequently removed from the peptide fragments. The peptide fragments are then analysed by MALDI-TOF mass spectrometry and the sequence of the fragments derived from the molecular mass of each fragment. The results are displayed quantitatively to indicate the relative quantity of each fragment. Where no Aβ protein or Aβ protein fragments are detected in the macrophages, this is indicative that the patient has AD.

The Aβ fragments shown in the IP-MS spectra result from intracellular degradation according to the character of the catalytic active site and conditions of action of intracellular protease/peptidases. Such fragments do not necessarily correspond to the sequences of Aβ fragments found extracellularly in CSF. Thus in some embodiments, in order to identify the exact length of each Aβ fragment obtained in the experiment, the peptides are isolated for determination of their respective amino acid sequences.

It is to be appreciated that the method described above detects the presence of the Aβ protein fragments that are present in vivo in the patient. The method does not involve a separate step of exposing the macrophages to the Aβ protein, in vitro, after extraction from the patient.

In some embodiments, the level of the Aβ protein fragments detected is compared with the level detected in a control individual who does not have AD. In such embodiments, a comparison is made between the level and pattern of Aβ protein fragments from the patient and those of the control individual. Where the level of Aβ protein fragments is significantly below that in the control individual then this is indicative of AD in the patient. Similarly, if the type of Aβ protein fragments present in the individual is significantly different from those in the control individual then this is indicative of AD in the patient. In alternative embodiments, a standard level of Aβ protein fragments is generated by detecting the presence of such fragments in the macrophages in CSF in a plurality of control individuals who do not have AD. The level and pattern of Aβ protein fragments from the patient is then compared with the standard level and a statistically significant reduction in level or difference in pattern of the presence of fragments is indicative of AD.

In other embodiments, a single patient is examined annually over a period of time (e.g. 10 years). On each occasion, the levels of Aβ protein fragments in the macrophages in a CSF sample from the patient is studied as described above. A significant change in the level or pattern of Aβ protein fragments each year, in particular a reduction in the level of the Aβ protein fragments year on year, is indicative of the presence of AD.

In certain embodiments, additional AD markers in the patient are also measured, at the same time as the above-described analysis is carried out. Such additional AD markers include abnormal levels of Aβ42, Tau, Phospho-Tau or the Aβ42/Aβ40 ratio in a CSF sample obtained from the patient or in the RNA profile of a blood or CSF sample obtained from the patient. An abnormal level of some or all of these additional AD markers as well as an abnormal level of Aβ protein fragments in the macrophages in the CSF of the patient is indicative of the presence of AD. An exemplary abnormal (i.e. pathological) level of Aβ42 is a CSF concentration of less than 550 pg/ml. The concentration of Tau is age-dependent, high levels being pathological. A pathological level of Phospho-Tau is a CSF concentration of greater than 85 pg/ml. A pathological level of the Aβ42/Aβ40 ratio is where (Aβ42/Aβ40)×10 is less than 1.

In the above described embodiments, a CSF sample from the patient is obtained. However, in alternative embodiments, a different type of sample is studied, for example, a blood sample. Such an alternative sample may be used because macrophages circulate from the bone marrow to the CNS and therefore macrophages in the blood of a patient may have been exposed to proteins in the CNS. It is, of course, easier to obtain a blood sample than a CSF sample from a patient.

One embodiment of the present invention uses the following criteria as the basis of a diagnostic test to assess Alzheimer's disease in a patient's activated macrophages/microglia: 1) Fulfilment of disease criteria, 2) Presence and sorting of CD16+ population of cells in CSF and blood with flow cytometry, 3) Presence/absence of Aβ peptide fragments in MS spectra after immunoprecipitation with antibodies, 4) Tailored methods at clinics. Flow cytometry and IP-MS can be replaced by other methods for sorting or distinguishing of cell subtypes and peptide fragment analysis.

Methods of Evaluating Fulfillment of Disease Criteria

The patient undergoes a thorough clinical investigation, including a study of medical history, physical, neurological and psychiatric examination, screening laboratory tests and MRI and PET imaging of the brain. The diagnosis of AD is made according to recently published criteria [12]. The patient undergoes a thorough physical and psychological examination when enrolled in the diagnosis programme at a hospital. The examination includes neuropsychological questionnaires for identification of cognitive deficits, neurological examination, genetic analysis, CSF biomarkers, imaging and metabolic profile.

Methods of Evaluating Presence and Sorting of CD16+ Population of Cells in CSF and Blood with Flow Cytometry Cells are acquired on a FACSAria Cell-Sorting System and analysed using FACSDiva software (both Becton Dickinson). CSF cell populations are sorted based on their expression of relevant surface markers (CDs). Cells are gated according to forward- and side light-scattering properties and are positively selected for the presence of CD45+CD3+CD4+CD8 (characterisation of T-cell population), and CD45+CD14+CD16+CD19 (characterisation of activated macrophages and B-cell population). In order to preserve the immune cells intact, the cell sorting is performed at a maximum of four hours post puncture. $CD14^+/CD16^+$ sorted cells are lysed and kept frozen at −80° C. for further analysis (protein-analysis). In addition to collecting cells for protein analyses, the flow cytometry results indicate the CSF and periphery (blood) immune cell distribution for the patient.

Method of Preparation of Cells for Immunoprecipitation

Figure 2:
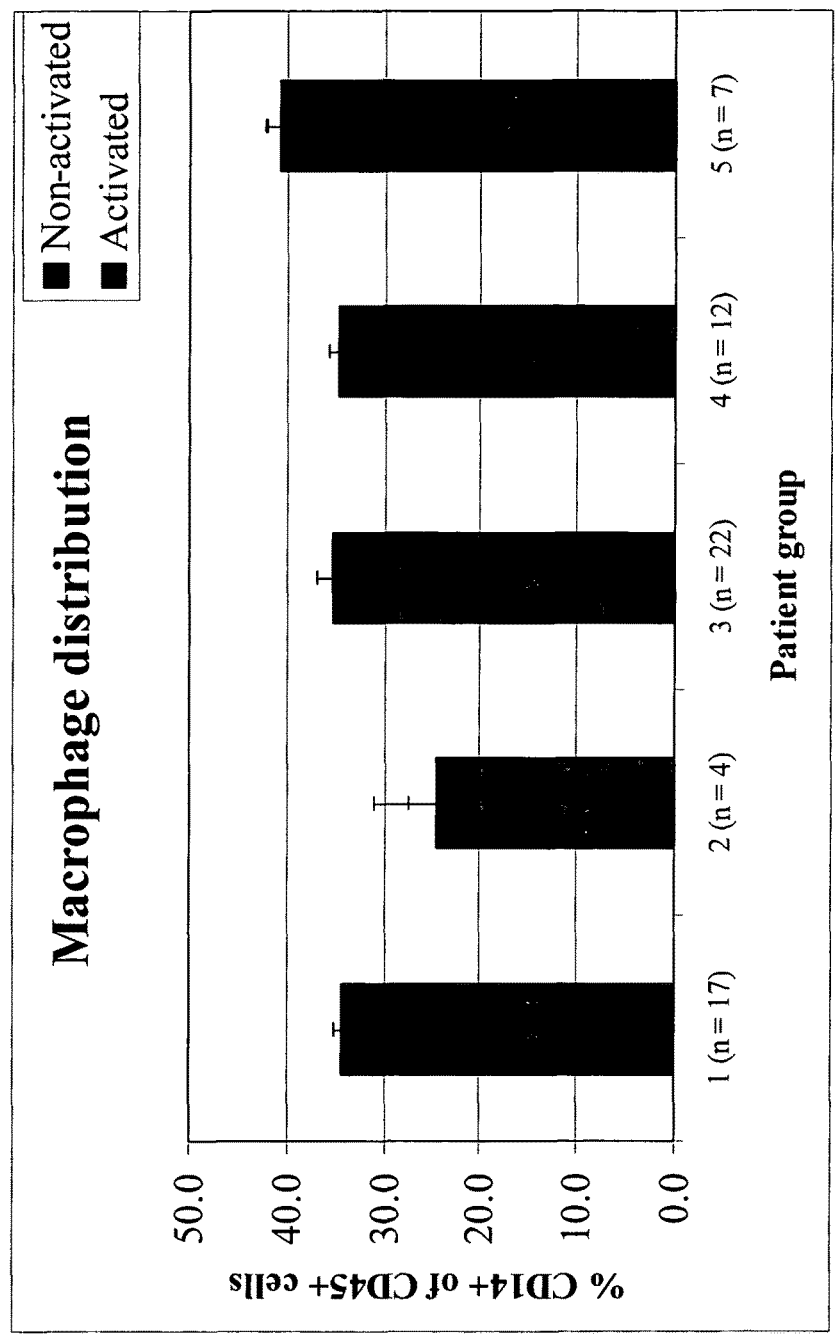
FIG. 2 is a graph showing the relative distribution of activated and non-activated macrophages from patients with 1: Alzheimer disease (AD), 2: Multiple sclerosis (MS), 3: no CNS disease, 4: MCI/non-AD and 5: 7-10 days post stroke.

CSF cell populations were sorted based on their expression of relevant surface markers (CDs). Cells were gated according to forward- and side light-scattering properties and were positively selected for the presence of CD45+CD3+CD4+CD8 (characterisation of T-cell population), and CD45+CD14+CD16+CD19 (characterisation of activated macrophages and B-cell population). Cell population and number of cells within each population were obtained and registered (see FIG. 2). The number of activated cells in 7-10 days post stroke patients is high, suggesting circulation of recruited cells also to the CSF compartment of a large number of immune cells. The number of activated macrophages in AD largely equals that in the MCI/non-AD group. The total of %-activated cells in MS is lower that AD; which may be because the immune process in MS mainly involves T-cells.

The sample $CD14^+/CD16^+$ and $CD14^+/CD16^-$ sorted cells were washed with 400 µl PBS and centrifuged (4° C., 750×g, 5 min). The supernatant was removed and prepared for IP-MS analysis by adding 10 µL RIPA-buffer for cell lysis and keeping frozen at −80° C. prior to protein-analysis.

Method of Immunoprecipitation

An aliquot (4 µg) of the monoclonal antibodies 6E10 (1 mg/mL, epitope 4-9), 4G8 (1 mg/mL, epitope 18-22), or 11A50-B10 (0.5 mg/mL, reactive to the C-terminus) (Signet Laboratories, Inc.) was separately added to 50 µL magnetic Dynabeads (Sheep anti mouse, IgG) and incubated overnight on a rocking platform at +4° C. The remaining unbound antibody was removed by washing twice with phosphate-buffered saline (PBS, pH 7.4). After adding 1 mL CSF to the antibody-coated beads, the incubation was continued for an additional 1 h at +4° C. The beads were pelleted for 5 min by using a magnetic particle concentrator (Dynal MPC) and washed twice with PBS (pH 7.4) and twice with 50 mM ammonium bicarbonate (pH 7.3). After the final wash, the extracted Aβ peptides were eluted by adding 20 µL 0.5% formic acid (FA) in water. After vortexing for 2 min in room temperature, the beads were pelleted using the magnetic particle concentrator and the supernatant was collected. The collected supernatant was dried down in a vacuum centrifuge and redissolved in 5 µL 0.1% FA in 20% acetonitrile (ACN). All solvents used were of HPLC quality and all aqueous solutions were made using 18.2 M deionized water obtained from a Millipore purification system.

Methods of Evaluating Presence/Absence of Aβ in MS Spectra after Immunoprecipitation IP-MS is used to isolate and determine the Aβ peptide content (Aβ signature) in the $CD14^+/CD16^+$ macrophages sorted by flow cytometry. Proteolytically processed Aβ peptides are difficult to detect using standard proteomic methods possibly because they comprise a heterogeneous set of both N- and C-terminally truncated peptides, some at low quantity. IP-MS analysis has been used previously to obtain an Aβ peptide signature successfully [43] [44] (see FIG. 6). Briefly, the Aβ peptides are isolated from lysed macrophages using anti Aβ monoclonal antibodies and magnetic Dynabeads. Then a matrix-assisted laser desorption/ionisation time of flight mass spectrometry (MALDI-TOF MS) analysis is performed on the immunoprecipitated peptides and the macrophage Aβ signature is calculated. The Absence of Aβ signal in the specimen is interpreted as a positive AD diagnosis.

Alternative Methodologies

In variants of the above-described methodology, the following techniques are used.
1. Instead of using flow cytometry to sort cells, activated macrophages/microglia cells are withdrawn using magnetic extraction, flotation techniques, or other antibody or affinity-based extraction techniques e.g. chromatography, gradient centrifugation. Alternatively the cells are studied using immunohistochemistry
2. Immune precipitation using other antibodies specific for the peptide/protein of interest.
3. Instead of using mass spectrometry, another technique for quantitative or semi-quantitative peptide/protein analysis is employed such as: HPLC-fluorescence or -UV, luminescence, streptavidin/biotin systems, immunohistochemistry a.o.

Alternative Conditions

In alternative embodiments a different pathological condition characterised by the presence of fragments of a marker protein in the brains of patients is studied. In each case it is necessary to identify the condition to be studied and the corresponding protein that characterises the condition. Exemplary conditions include: Parkinson's Disease in which ubiquitin (SEQ. ID NO: 2) is the characterising protein; Multiple Sclerosis where myelin basic protein (SEQ. ID NO: 3) characterises the condition; FrontoTemporal Dementia and Amyotrophic Lateral Sclerosis which are characterised by the tau protein (SEQ. ID NO: 4); and Parkinson's Disease (SEQ. ID NO: 5), Lewy body dementia and AD which are characterised by the alpha-synuclein protein. In each case, the method of detection or monitoring is carried out as is described above in relation to AD except that the antibodies used to immunoprecipitate the peptides from the macrophages are substituted with antibodies that are capable of binding fragments of the characterising protein of the condition. Furthermore, in the case of Multiple Sclerosis, abnormally high levels of the ubiquitin marker protein are indicative of the presence of the condition.

In some embodiments, multiple such conditions are tested for simultaneously by immunoprecipitating cell lysates with multiple sets of antibodies, each set of antibodies being specific for fragments of different characterising proteins.

In some embodiments of the invention, a diagnostic kit is provided in order to enable the detection of a pathological condition of the invention (that is to say a condition characterized by the presence of fragments of a marker protein in the brain of a patient suffering from the condition). The kit is suitable for use in ordinary clinical laboratories since it is based on an ELISA/immuno-PCR technique and so does not require the use of MALDI-TOF or IP-MS techniques as described in some previous embodiments. The kit comprises a panel of target specific antibodies which are specific for a first epitope of the marker protein. Thus, for example, where the pathological condition to be detected is Alzheimer's disease, the marker protein is the Abeta 42 protein. The kit also comprises a supply of magnetic beads which display macrophage specific antibodies (for example, antibodies specific for the CD14 and CD16 cell markers); a cell lysing agent such as RadioImmuno Precipitation Assay (RIPA) Buffer containing 25 mM Tris-HCl pH 7.6, 150 mM NaCl, 1% NP-40, 1% Sodium deoxycholate and 0.1% SDS (Pierce Biotechnology); and a secondary antibody which is specific for a second epitope of the marker protein. The secondary antibody is conjugated to a double-stranded DNA marker molecule.

Figure 8:
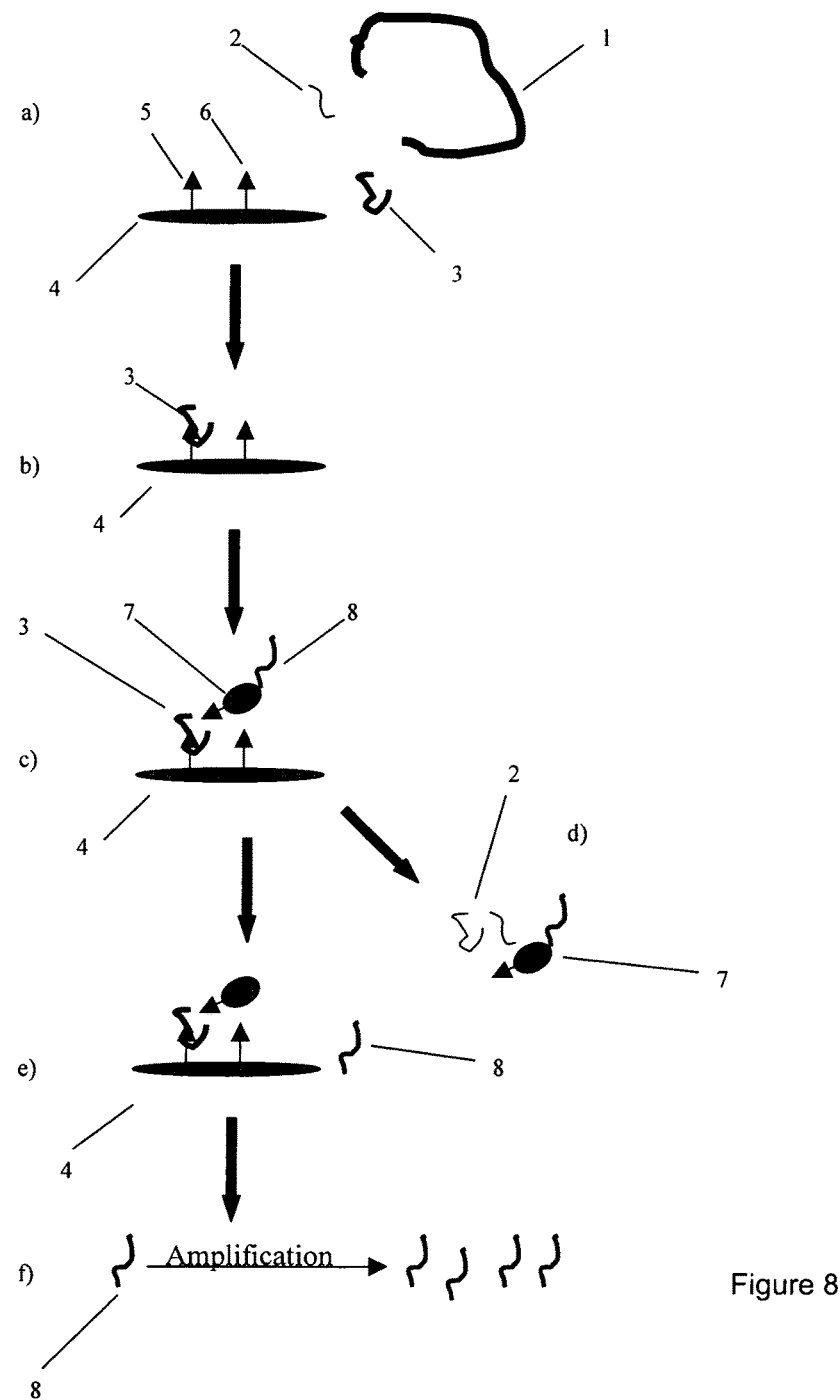
FIG. 8 is a schematic diagram of a kit in accordance with one embodiment of the present invention, in use.

Referring to FIG. 8, the kit will now be described in use. A sample, such as a peripheral blood or CSF sample, is obtained from a patient and macrophage cells are isolated from the sample by mixing with the magnetic beads provided in the kit. The macrophage specific antibodies displayed by the magnetic beads bind the macrophages in the patient sample and the macrophages and the magnetic beads are then removed from the sample by magnetic means. The macrophage cells are then released from the macrophage specific antibodies by adjusting the pH of the solution and the macrophage cells 1 are lysed with the lysing agent in order to release the cell contents 2 which includes the marker protein 3 as shown in FIG. 8A.

Also provided in the diagnostic kit is a solid support 4 on which are immobilised a plurality of target antibodies 5, 6 which are specific for the marker protein 3.

As shown in FIG. 8b, the contents 2, 3 of the lysed macrophage cell 1 are then contacted with the solid support 4 such that the first epitope of the marker protein 3 binds to the target antibody 5.

Referring to FIG. 8c, the solid support 4 is contacted with a secondary antibody 7 which is conjugated to a double-stranded DNA marker molecule 8. The secondary antibody 7 is specific for the second epitope of the marker protein 3 such that the secondary antibody 2 is immobilised on the solid support 4 where the marker protein 3 is present.

Unbound proteins and unbound secondary antibody are then washed out and removed (see FIG. 8d).

Referring to FIG. 8e, the washed solid support 4 is then subjected to real time PCR which melts the double stranded DNA marker molecule 8 and amplifies the copy number (see FIG. 8f) in order to identify the number of copies of the DNA marker molecule. The number of copies of the DNA marker molecule 8 after a predetermined number of cycles of PCR amplification is indicative of the starting number of DNA molecules. Furthermore, there is a one-to-one relationship between the starting number of DNA molecules and the number of bound marker proteins. Therefore, this immuno-PCR technique provides an accurate indication of the number of marker protein molecules in the patient sample.

Accordingly, such diagnostic kits allow a simple immunological method to be used in standard clinical laboratories which are available in all hospitals, private clinics and commercial laboratories in order to analyse patient samples in accordance with the present invention. The use of the kit of the invention does not require the use of expensive or advance laboratory instruments and detection using an immuno-PCR technique ensures high sensitivity.

Figure 9:
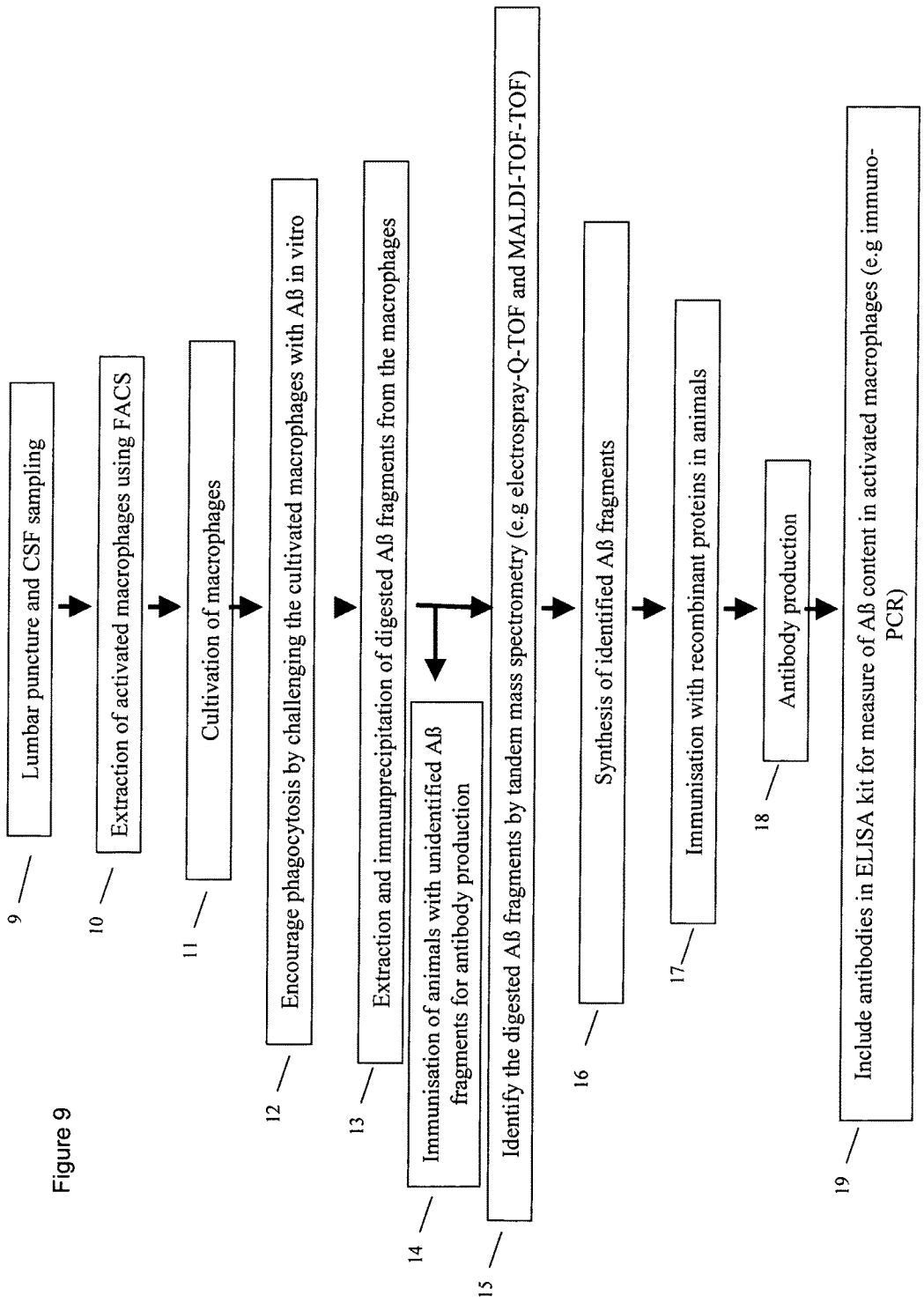
FIG. 9 is a flow diagram showing the steps in the production of antibodies for use in a kit in accordance with one embodiment of the present invention.

The target antibodies of the diagnostic kit may be antibodies already known in the art which are capable of binding the marker protein, such as the antibodies 6E10, 4G8 and 11A50-B10 described above. However, further antibodies can be identified as is explained in the flow chart in FIG. 9 in relation to antibodies to the Abeta protein. The process begins with obtaining a suitable patient sample by extracting a cerebral spinal fluid sample by a lumbar puncture (box 9).

Subsequently, the activated macrophages from the sample are extracted by binding of labelled antibodies to suitable cell markers (e.g. CD14 and CD16) in the patient sample and sorting of the cells by FACS (see box 10). The isolated macrophages are then cultivated (box 11) and are encouraged to phagocytosis by challenging with the Abeta protein in vitro (box 12). Further details of this step are provided in the "amyloid-beta stress test" of Fiala et al (39). The cultivated macrophages are then lysed and digested fragments of the Abeta protein are extracted and immunoprecipitated (box 13).

At this stage in the procedure, the Abeta fragments may, themselves, be used to immunise host animals (such as rabbits) in order to produce antibodies specific for the Abeta protein fragments on a small-scale (box 14). However, for larger scale production of antibodies, the procedure continues with the identification of the digested Abeta protein fragments using tandem mass spectrometry (e.g. electrospray-Q-TOF or MALDI-TOF (box 15)). Once the sequences of the Abeta protein fragments have been identified, the fragments are synthesised, for example by recombinant expression in a host cell such as $E.\ coli$ (box 16). The synthesised Abeta protein fragments are then used to immunise host animals (usually rabbits) (box 17) which in turn produce antibodies (box 18). Antibodies may be obtained from the host animals and included in the diagnostic kits, but preferably, monoclonal antibody-producing cells are produced, as is known in the art (e.g. by production of hybridoma cells). Alternatively, the antibodies, or at least their complementarity determining regions, are sequenced and recombinantly expressed. Whichever method of antibody production is selected, the antibodies are purified and included in the diagnostic kit (box 19).

In some variants of the above-described diagnostic kits, a plurality of panels of antibodies are provided in the kit. For example, in one variant, the kit comprises first target antibodies that are specific for a first epitope of the Abeta protein and second target antibodies which are specific for a third epitope of the Abeta protein. In still further embodiments, a plurality of panels of antibodies are provided in the kit and the antibodies are specific for marker proteins corresponding to more than one pathological condition. For example, in one particular variant, a panel of antibodies is provided which is specific for the Abeta protein (the marker protein for Alzheimer's disease) and a panel of antibodies is provided specific for Multiple Sclerosis (where myelin basic protein is the marker protein). In these variants, it is preferred that different panels of secondary antibodies, each specific for a respective marker protein and each conjugated to a different DNA marker molecule, are provided such that the signal for the detection of each marker protein is distinguishable.

In the above described embodiments of the diagnostic kit, the detectable label is a DNA marker molecule. However, in other embodiments, a different detectable label is used. For example, the detectable label may be a fluorophore, a latex microbead or a gold particle. Such alternative detectable labels are useful when the kit is provided only to provide a qualitative result rather than a quantitative result.

In some alternative embodiments of the kit, a lysing agent, as such, is not provided. Instead, cells are lysed mechanically, e.g. by centrifugation, prior to isolation of the macrophages.

It is also to be appreciated that the diagnostic kits of the present invention are not limited to kits comprising antibodies. In alternative embodiments, the antibodies of the kit are replaced with other binding reagents such as antigen binding fragments (e.g. F(ab')$_2$ fragments or Fab fragments) or a polynucleotide sequence. Typically such other binding reagents have binding affinities for their target comparable to that of antibodies such as having a binding affinity of less than 100 nm in an aqueous buffered solution at between pH 4 and 8.

EXAMPLES

Example 1

Patient Selection

Patients were ambulatory or intramural and were recruited from Nevroklinikken at Akershus University Hospital. Lumbar puncture was performed as a planned procedure. The patient groups were divided into following diagnosis: 1) probable Alzheimer's disease (AD) diagnosed according to NINCS-ADRA criteria [12]; 2) probable Multiple sclerosis (MS) diagnosed according to the McDonald criteria; 3) no nervous system disease (e.g. ME, and other patients with a full negative investigation for "organic" disease); 4) mild cognitive impairment (MCI)/non-AD; and 5) 7-10 days post-stroke patients.

Example 2

Lumbar Puncture/Blood Sampling

The lumbar puncture was routinely carried out in connection with diagnosis between 0900 and 1330 hrs. CSF was obtained from patients through lumbar puncture between vertebras L4 and L5 with the patients in horizontal positions. The skin in the lumbar region was thoroughly washed with sterile cotton swabs and chlorhexidine 5%. The neurologist on call performed the lumbar puncture. Fine disposable needles were used (Becton Dickinson 20GA 3.5 IN 0.9×90 mm). The sample for flow cytometry analysis was collected as the final sample, altogether 2 mL (~40 droplets) of CSF. The blood sample (EDTA or heparin) was taken immediately prior to or following the lumbar puncture.

Cells were acquired on a FACSAria Cell-Sorting System and analysed using FACSDiva software (both Becton Dickinson) within a maximum of four hours post puncture/blood sampling.

Example 3

Preparation and Analysis of CSF/Blood Samples by Flow Cytometry 2 mL CSF and/or 4 mL blood was pelleted (4° C., 400×g, 10 min). The supernatant was removed and the remaining cell pellets were washed once with staining buffer (Becton Dickinson, San Jose, Calif.). The cell pellets were diluted in 1-2 mL of staining buffer and were centrifuged at 4° C., 400×g, 10 min. The supernatant was removed, and the sample was transferred to a flow tube. The sample was stained with a panel of fluorescent-labelled antibodies (2.5 μL CD4-FITC and CD19-FITC, 2.0 μL of CD8-PE, CD16-PE and CD45-PerCP, 1.5 μL CD3-APC and CD14-APC all from Becton Dickinson). The samples were incubated in a refrigerator for 15-20 minutes before adding 3-4 droplets of FACSFlow solution, mixed and made ready for flow cytometry analysis.

Example 4

Flow Cytometry Analysis and Cell Sorting

CSF cell populations were sorted based on their expression of relevant surface markers (CDs). Cells were gated according to forward- and side light-scattering properties and were positively selected for the presence of CD45+ CD3+CD4+CD8 (characterisation of T-cell population), and CD45+CD14+CD16+CD19 (characterisation of activated macrophages and B-cell population). Cell population and number of cells within each population were obtained and registered (see FIG. 2). The number of activated cells in 7-10 days post stroke patients is high, suggesting circulation of recruited cells also to the CSF compartment a large number of immune cells. The number of activated macrophages in AD largely equals that in the MCI/non-AD group. The total of %-activated cells in MS is lower that AD; which may be because the immune process in MS mainly involves T-cells.

The sample $CD14^+/CD16^+$ and $CD14^+/CD16^-$ sorted cells were washed with 400 µl PBS and centrifuged (4° C., 750×g, 5 min). The supernatant was removed and prepared for IP-MS analysis by adding 10 µL RIPA-buffer for cell lysis and keeping frozen at −80° C. prior to protein-analysis.

Example 5

Pooling of Patients According to Diagnosis

The sorted cells were pooled together according to diagnosis, prior to IP-MALDI-TOF-MS analysis, in the following groups.
1) Alzheimer patients: N=10 (F=8), Mean age=68,9, #CD16+ ~1894 cells
2) MS patients: N=3 (F=2), Mean age=45, #CD16+ ~773 cells
3) No CNS disease, N=13 (F=8), Mean age=36,15, # CD16+ ~4792 cells
4) MCI/non-Alzheimer: N=5 (F=3), Mean age=71,4, # CD16+ ~1082 cells
5) 7-10 days post stroke N=5 (F=0), Mean age=67, # CD16+CSF~2930, #CD16+ blood~3748 cells

Example 6

Immunoprecipitation-Matrix-Assisted Laser Desorption/Ionisation Time of Flight Mass Spectrometry (IP-MALDI-TOF-MS)

Figure 3:
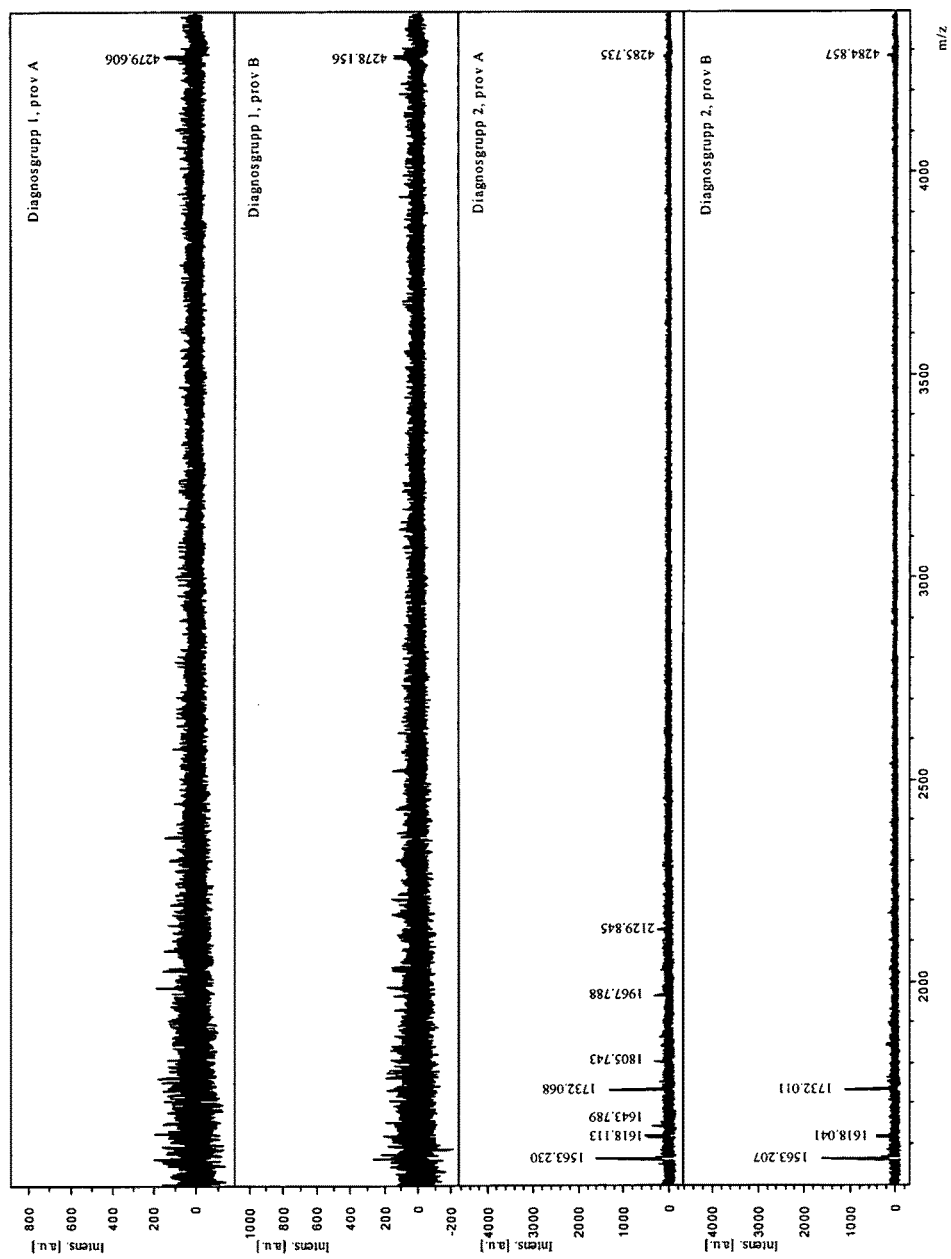
FIG. 3 shows IP-MS spectra of Aβ peptide fragments from CSF samples from patients. The two upper spectra are from AD patients, N=10 (F=8), Mean age=68.9, #CD16+ ~1894 cells. The two lower spectra are from MS patients, N=3 (F=2), Mean age=45, #CD16+ ~773 cells.
Figure 4:
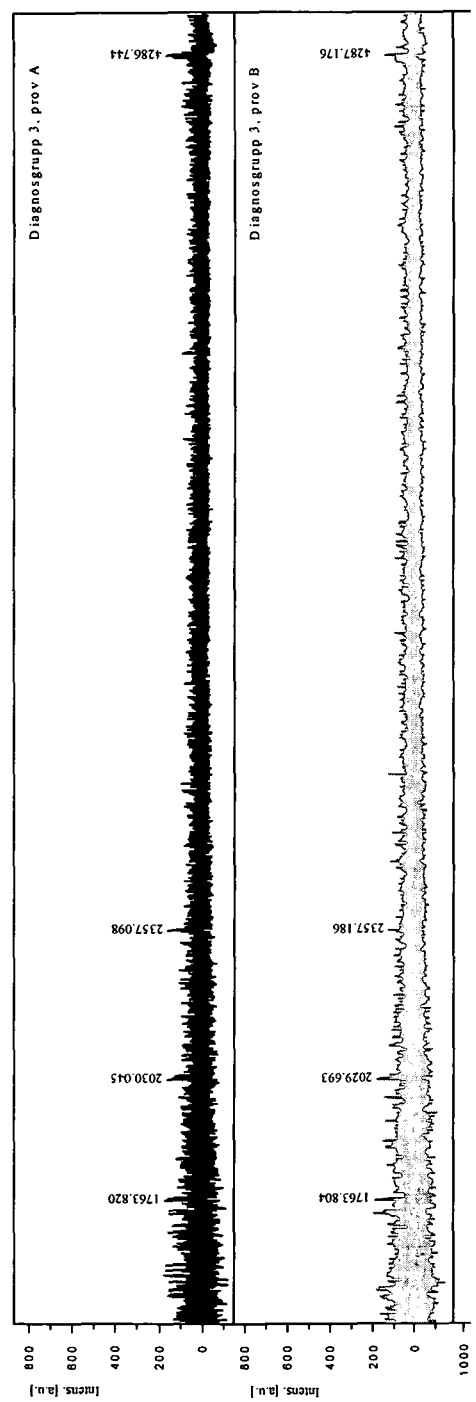
FIG. 4 shows IP-MS spectra of Aβ peptide fragments from CSF samples from individuals. The spectra are from individuals with no CNS disease, N=13 (F=8), Mean age=36.15, # CD16+ ~4792 cells
Figure 5:
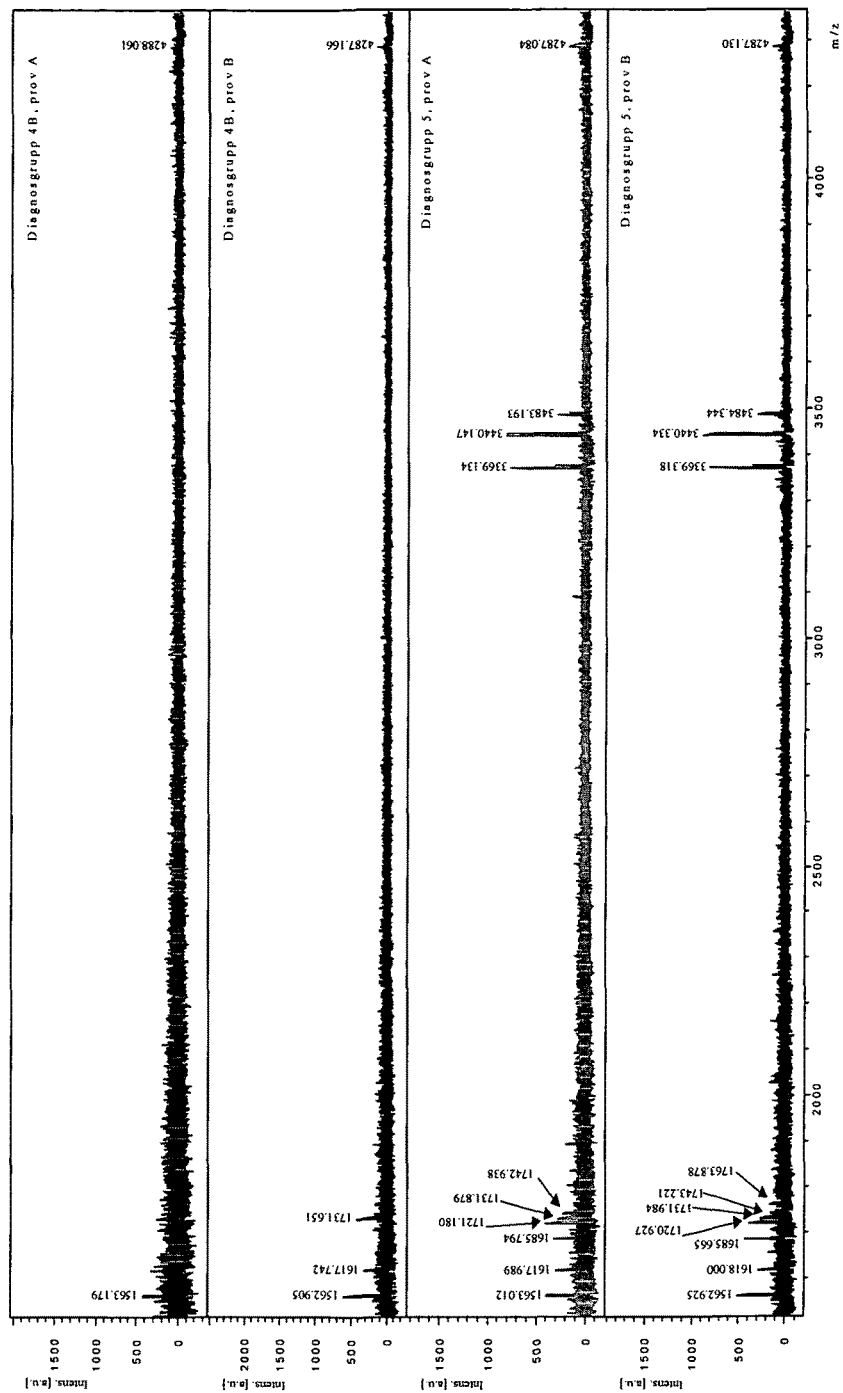
FIG. 5 shows IP-MS spectra of Aβ peptide fragments from CSF samples from patients. The two upper spectra are from patients with MCI but without AD, N=5 (F=3), Mean age=71.4, # CD16+ ~1082 cells. The two lower spectra are from patients 7-10 days post stroke, N=5 (F=0), Mean age=67, # CD16+ CSF~2930, #CD16+ blood~3748 cells.

Samples were immunoprecipitated as described above. MALDI samples were prepared with the seed layer method. Briefly, a seed layer was created on a MALDI-TOF MS stainless steel sample probe (Bruker Daltonics Inc.) by depositing 0.5 µL (1 g/L) of alfa-cyano-4-cinnamic acid (CHCA, Fluka) dissolved in ACN. One microliter of saturated (15 g/L) CHCA in 0.1% trifluoroacetic acid in ACN/water (1:1 v/v) was added to an equal volume of the dissolved peptides and mixed. One microliter matrix/peptide solution was added to the probe and the sample was left to dry completely in air. MALDI-TOF MS measurements were performed using an AUTOFLEX instrument (Bruker Daltonics Inc.) operating in reflecting mode at 19 kV acceleration voltage. The spectra represent an average of 900 shots and were recorded up to 4600 Da. The spectra were calibrated using internal calibration (m/z 1826.8, 2068.0, 4130.0, and 4328.2) and each sample was analyzed in duplicate. All mass spectra were analyzed using Bruker Daltonics flexanalysis 2.4, baseline subtracted and then smoothed with a 5-point Savitsky-Golay smooth. The results are shown in FIGS. 3 to 5, with two mass spectra per sample.

The results using IP-MS which are reported herein show that Aβ peptide fragments can be measured in activated macrophage/microglia subgroups, and differences in Aβ peptide content are related to disease type even though activated macrophage/microglia cells are present in normal numbers. Furthermore, the results show Aβ peptide fragments in macrophages/microglia in all control- and patient groups (the MS group, no CNS disease group and 7-10 days post stroke group) except AD patients, which show no detectable signal in the Aβ mass spectra (FIGS. 3 to 5).

These results suggest that despite having a distributed serious brain disease, the macrophage/microglia system in AD patients is not significantly activated compared with patients with no organic brain disease and post-stroke patients (compare groups 1, 3 and 5 in FIGS. 2 to 5). Furthermore, in contrast to all other patient groups, activated AD macrophage/microglia cells do not contain Aβ peptide fragments which indicates that their ability to phagocytose Aβ peptides is impaired or absent altogether.

Figure 6:
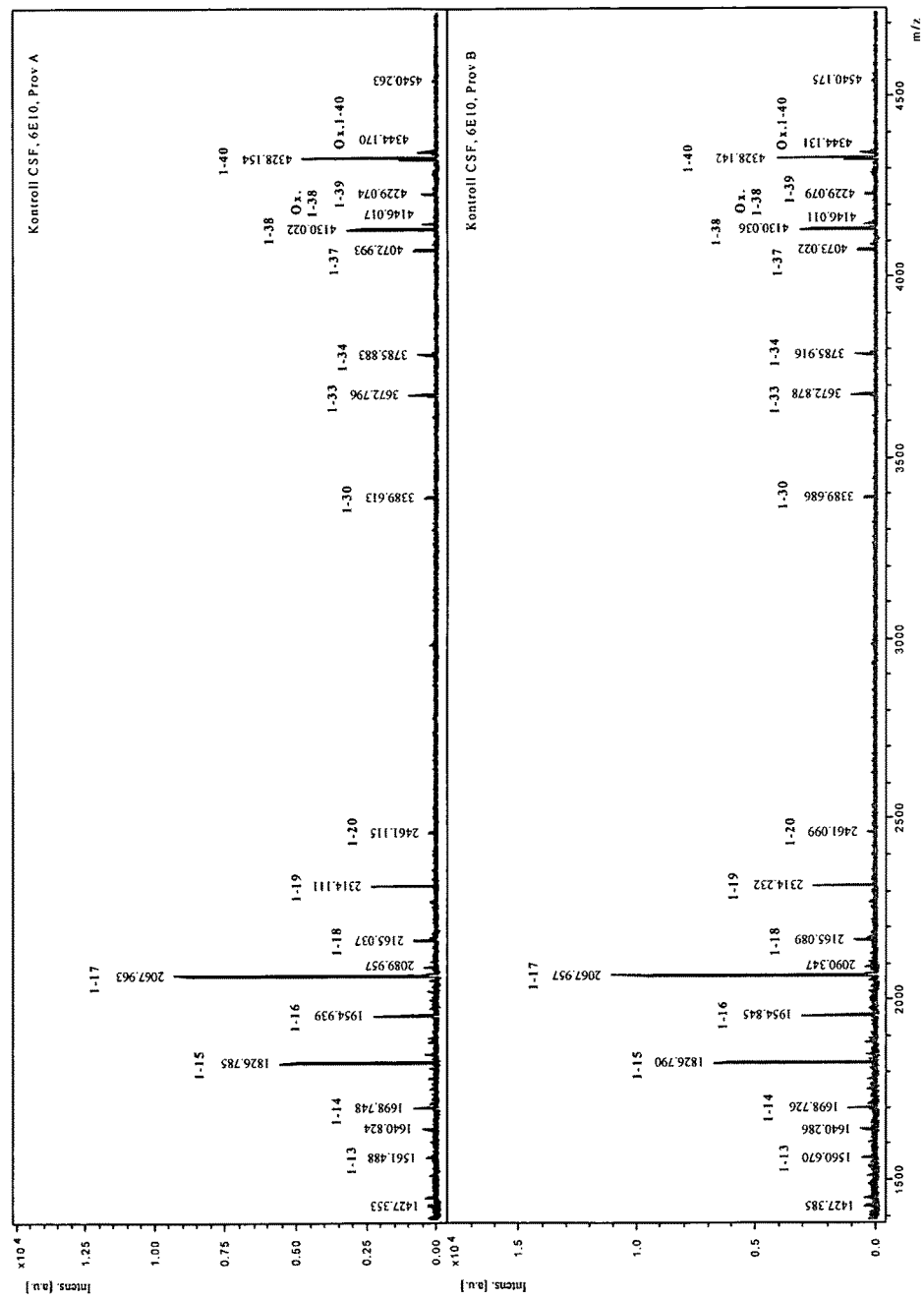
FIG. 6 shows IP-MS mass spectra of C- and N-terminally truncated Aβ peptides immunoprecipitated from CSF.

The Aβ peptide content of macrophages in non-AD individuals does not correspond to the normal Aβ protein degradation pattern in CSF that arises from excision of APP by amyloidogenic proteases, β- and γ-secretase (see FIG. 6). The different degradation patterns seen in macrophages from CSF and blood (see FIGS. 3 to 5) may result from proteolysis of Aβ protein within the macrophages. The results disclosed herein are based on 62 patients (see FIG. 2).

Example 7

Ultrastructure (Filtrating/SEM)

Scanning electron microscope (SEM) analysis of CSF CD14+/CD16+ sorted macrophages is used as a complement to flow cytometry, IP-MS and other techniques, in order to obtain an overall picture of morphology of activated macrophages versus non-activated macrophages. Putative infectious agents, other cells and debris in the CSF are visualized with this technique.

Untreated CSF, and the sorted cell solutions (selected according to $CD14^+/CD16^+$ and $CD14^+/CD16^-$ properties) containing activated and non-activated macrophages, are applied on to the surface of a polycarbonate 0.6 nm filter (Nucleopore, Inc), fitted to an airtight gadget (Gislaved, Sweden), vacuum filtered and immediately coated with a 40 Å thick layer of ionised gold for SEM. SEM is performed using a Philips High Resolution SEM (515). The morphology of these cells implies an active phagocytic status.

Example 8

Figure 7:
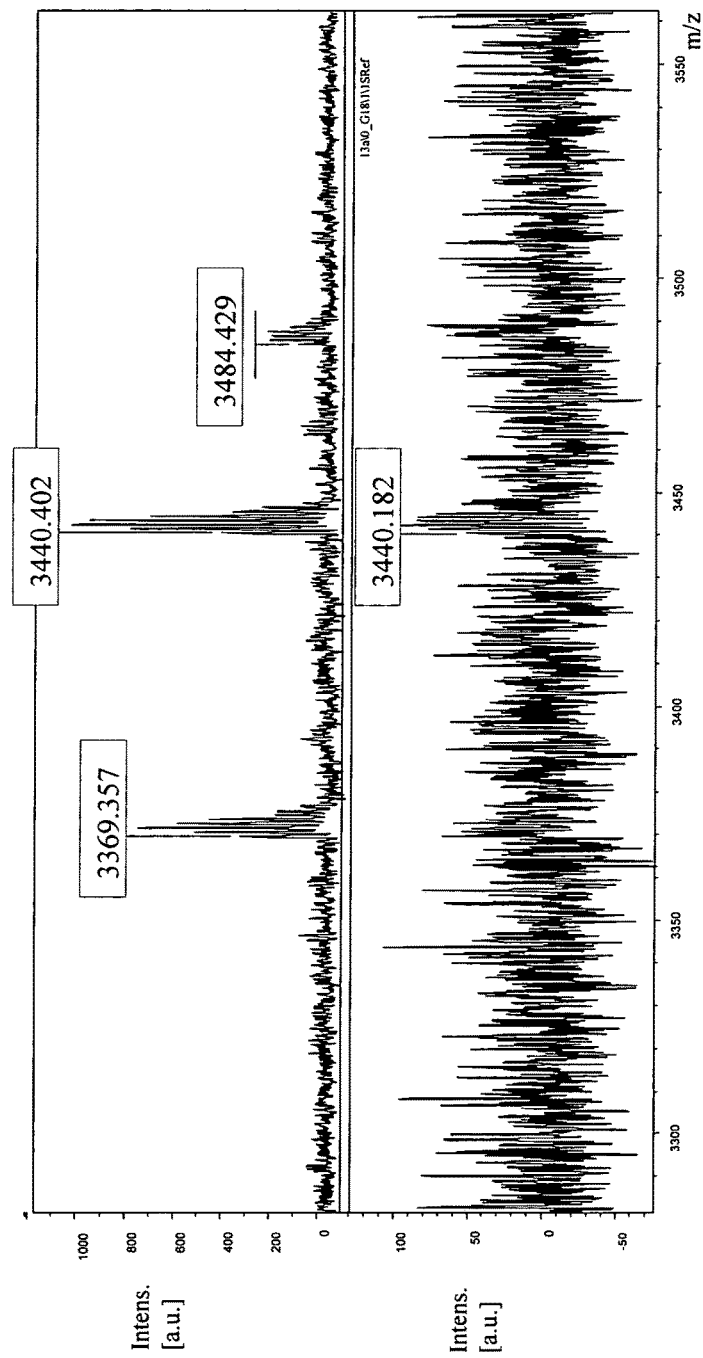
FIG. 7 shows IP-MS spectra of Aβ peptide fragments from peripheral blood samples from 7-10 days post stroke patient ($CD16^{++}$ upper spectrum and $CD16^{-}$ lower spectrum).

The procedures of Examples 1 to 4 and 6 were repeated with respect to peripheral blood samples obtained from a 7-10 days post stroke patient. However, there was no pooling of patients. IP-MS spectra were generated in order to detect the presence of Aβ peptide fragments. The spectra are shown in FIG. 7.

The upper spectrum shows $CD16^{++}$ cells from peripheral blood. The number of $CD16^{++}$ blood cells was 137. The peaks shown in this spectrum appear identical to the results shown in FIG. 5, lower spectrum (although the sample is drawn from a different patient). The lower spectrum in FIG.

7 shows CD16⁻ cells from peripheral blood from one patient without Aβ pathology. The number of CD16⁻ blood cells was ~35,000.

This example demonstrates that blood samples of a patient can be analysed in order to assess the phagocytosis of Aβ peptides by macrophages.

Example 9

Intracellular Staining of Macrophages from Patient with Probable Multiple Sclerosis with Anti Myelin Basic Protein (MBP) Antibodies Approximately 4.5 mL cerebrospinal fluid and 4.5 mL peripheral blood from a patient with probable Multiple Sclerosis were pretreated according to Example 3 before staining the cells with CD14-APC surface antibodies. Thereafter the cells were fixed and permeabilized with a formaldehyde/saponin-based reagent (IntraPrep) from Beckman coulter. The cells from CSF and blood were divided into 3 aliquots each and stained intracellularly with two different anti-myelin basic protein (MBP) antibodies from Epitomics (UniProtID P02686) and from Sigma (corresponding to residues 102-116 of human MBP). A non-specific isotype specific antibody (Rabbit IgG) from Epitomics was used as a control. In addition a sample with only CD14-APC staining was included. A secondary antibody (goat anti-rabbit IgG) from Invitrogen, fluorescently labeled with AlexaFluor488, was used to detect binding of primary antibody to antigen.

Flow cytometry was performed as described in Example 4. Cells were sorted according to their CD14⁺/intracellular signal, spotted onto a glass slide coated with polysine that attracts and adheres to cells. ProLong Gold antifade reagent (Invitrogen) was added to the slides (a mounting medium with DAPI), which enhances resistance to photobleaching and gives an additional staining of nucleus. A Leica confocal microscope was used to visualize cells.

Figure 10B:
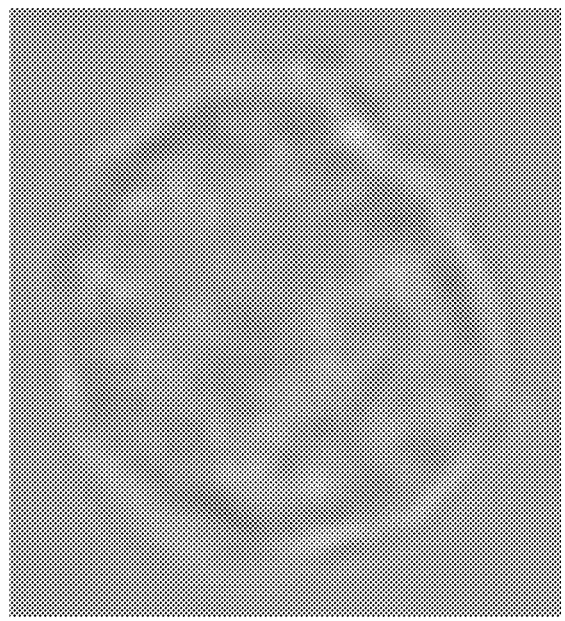
FIG. 10a is a fluorescent image of the cell and FIG. 10b is a transilluminated image of the same cell.
Figure 10A:
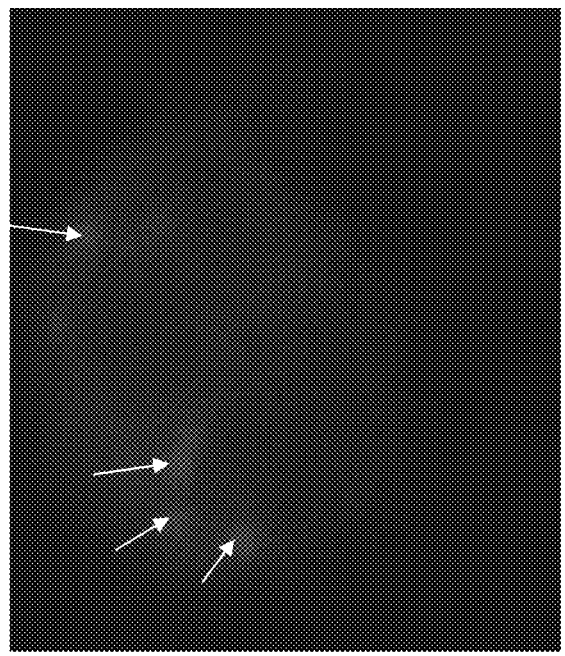

FIGS. 10a and b show a macrophage from CSF stained for intracellular MBP. Granular structures stained positive for MBP (white arrows).

Figures 11A, 11B:
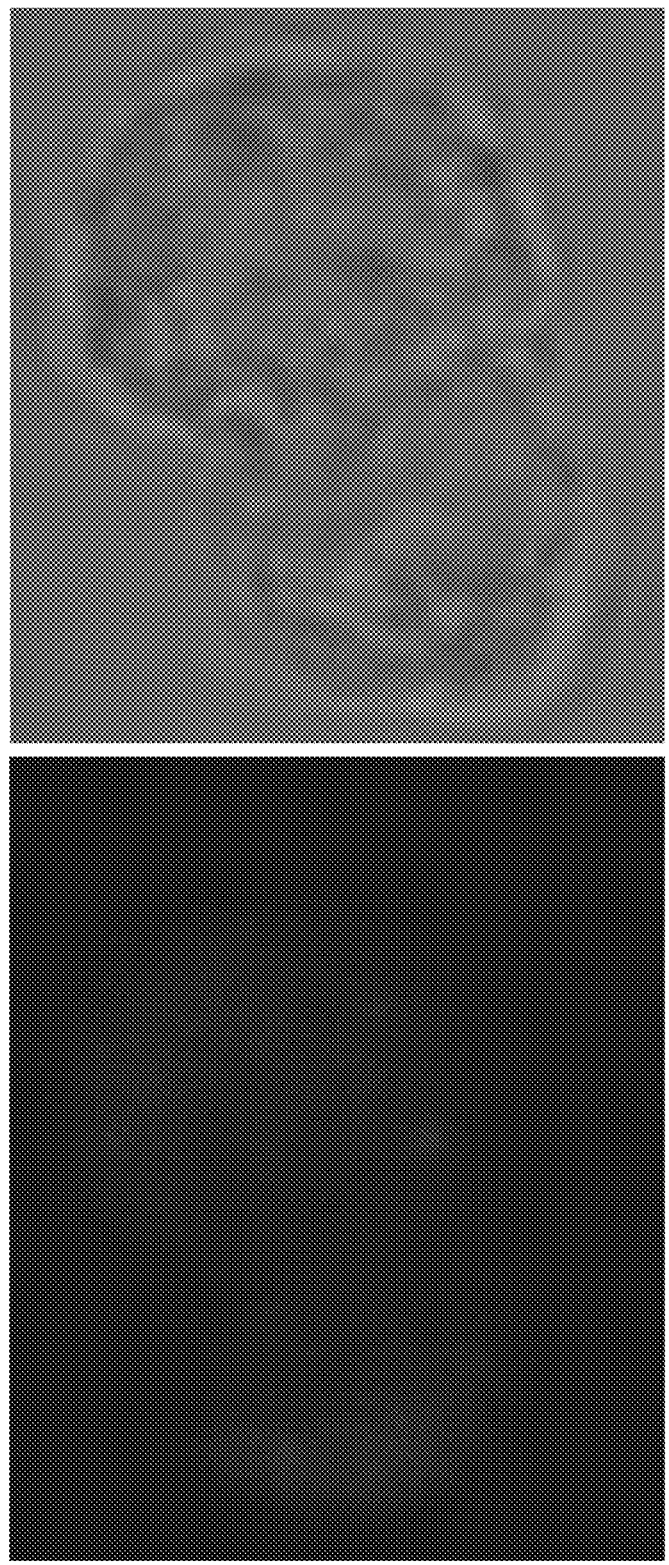
FIG. 11a is a fluorescent image of the cell and FIG. 11b is a transilluminated image of the same cell.

FIGS. 11a and b show a macrophage from CSF stained with isotype specific antibody control.

Figure 12B:
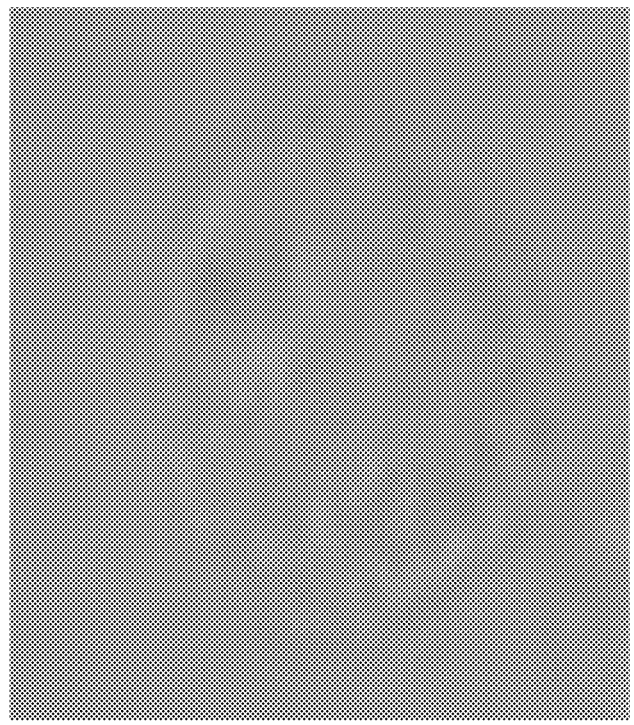
FIG. 12a is a fluorescent image of the cell and FIG. 12b is a transilluminated image of the same cell.
Figure 12A:
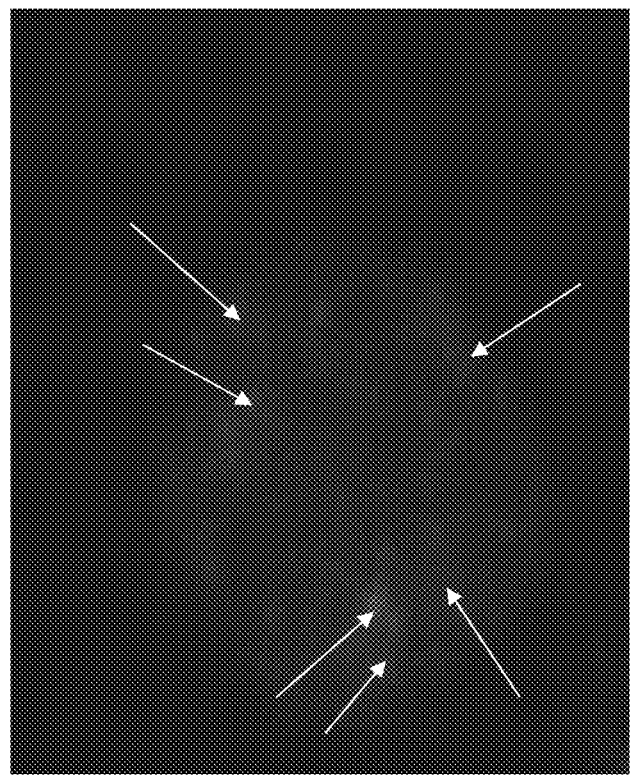

FIGS. 12a and b show a macrophage from blood stained for intracellular MBP. Granular structures stained positive for MBP (white arrows).

Figure 13B:
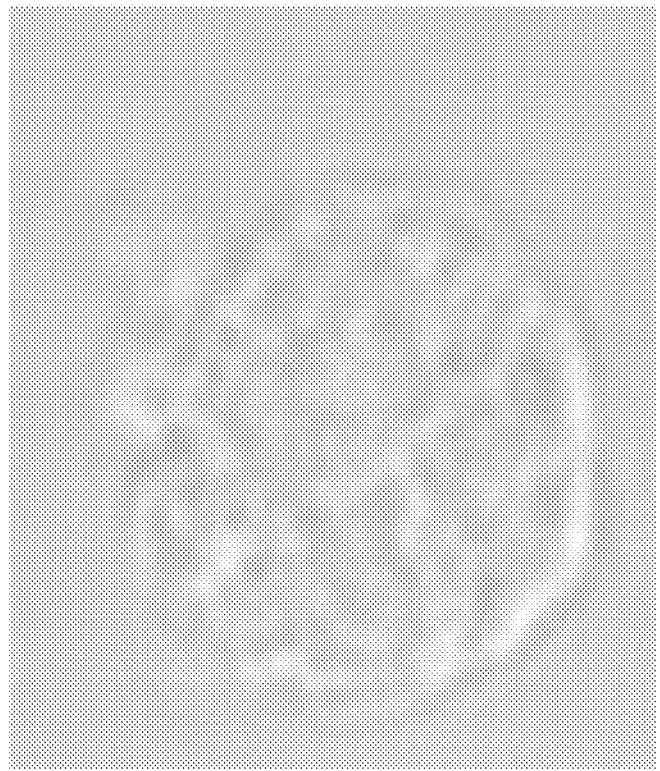
FIG. 13a is a fluorescent image of the cell and FIG. 13b is the transilluminated image of the same cell.
Figure 13A:
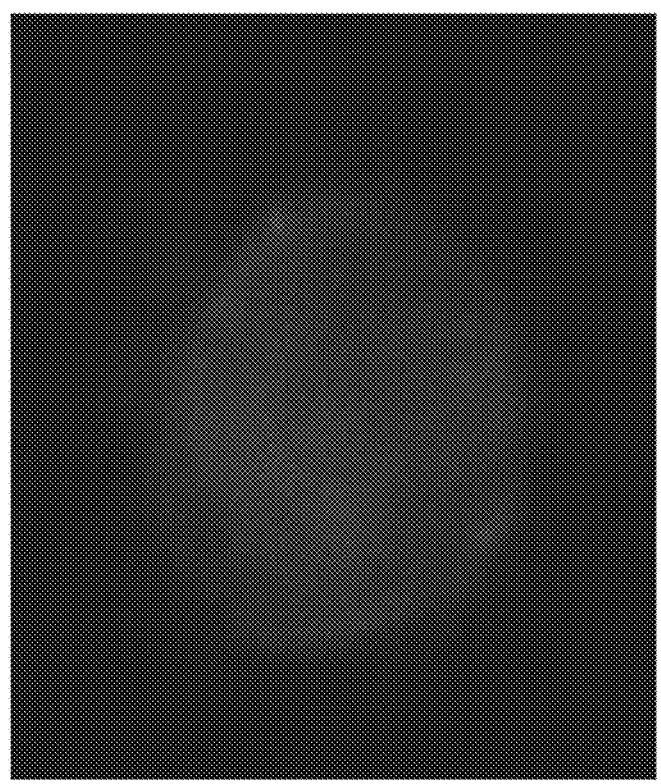

FIGS. 13a and b show a macrophage from blood stained with isotype specific antibody control.

Figures 14A, 14B:
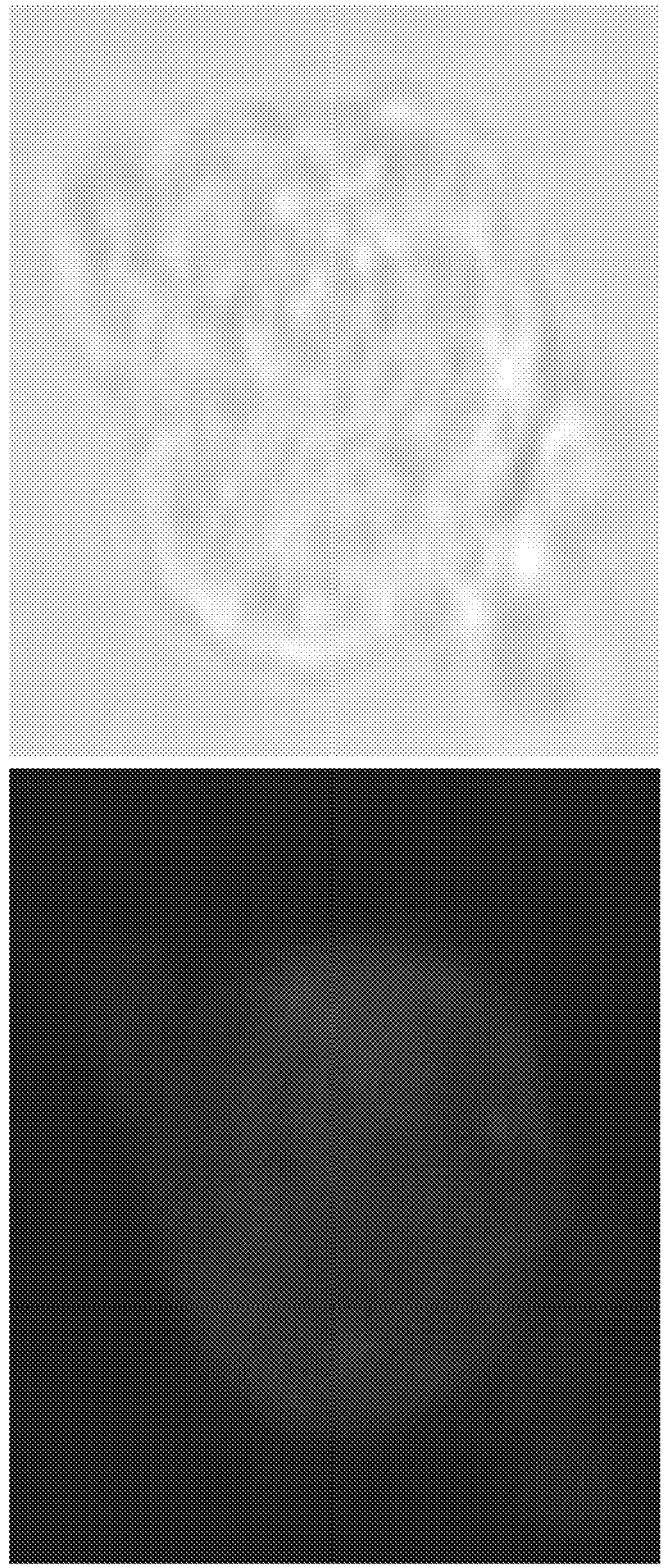
FIG. 14a is a fluorescent image of the cell and FIG. 14b is a transilluminated image of the same cell.

FIGS. 14a and b show a macrophage from blood with no primary antibody against intracellular antigens. The fluorescent signal is due to autofluorescense.

Figure 15A:
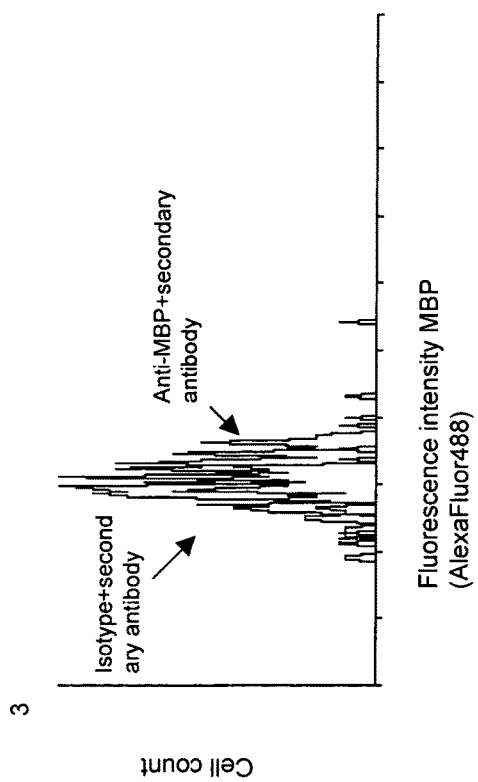
FIG. 15 shows graphs of Means Fluorescent Intensity in CSF (a) and Blood (b) against cell count.
Figure 15B:
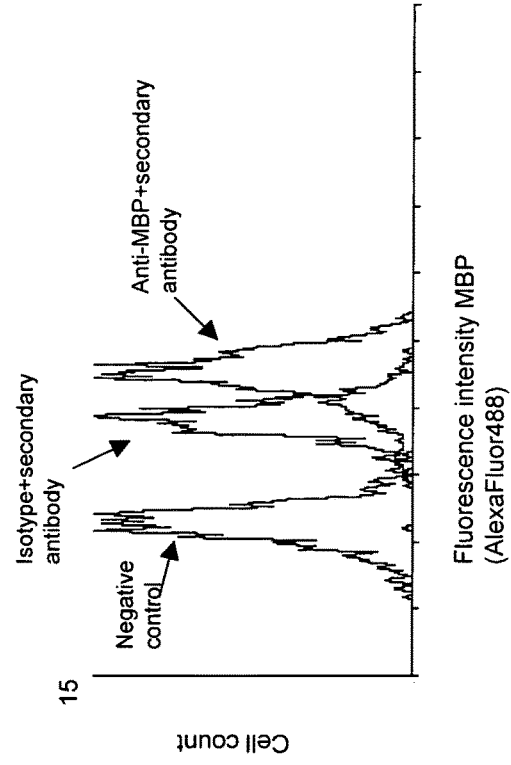

FIGS. 15a and b shows Mean Fluorescent Intensity (MFI) in CSF(a) and blood(b) from a patient with suspected MS. A MFI difference between the cells stained with MBP and cells stained with isotype specific antibody and a negative control (no primary antibody against intracellular antigens) is shown suggesting presence of bound anti-MBP giving an AlexaFluor 488 signal in the flowcytometer. Tabulated results are provided in Tables 1 (CSF) and 2 (peripheral blood).

TABLE 1

| CSF | Number of macrophages | Mean FI | Geometric Mean FI | CV |
|---|---|---|---|---|
| Rabbit Anti MBP | 135 | 402 | 376 | 36.1 |

TABLE 1-continued

| CSF | Number of macrophages | Mean FI | Geometric Mean FI | CV |
|---|---|---|---|---|
| Rabbit Isotype control | 104 | 328 | 292 | 98.9 |

TABLE 2

| PB | Number of macrophages | Mean FI | Geometric Mean FI | CV |
|---|---|---|---|---|
| Rabbit Anti MBP | 767 | 1503 | 1419 | 32.07 |
| Rabbit Isotype control | 1036 | 783 | 766 | 19.8 |
| Negative control | 1340 | 169 | 163 | 30.7 |

REFERENCES

1. Almberg, B., M. Grafstrom, and B. Winblad, *Caring for a demented elderly person—burden and burnout among caregiving relatives*. J Adv Nurs, 1997. 25(1): p. 109-16.
2. Beeson, R., et al., *Loneliness and depression in caregivers of persons with Alzheimer's disease or related disorders*. Issues Ment Health Nurs, 2000. 21(8): p. 779-806.
3. Jonsson, L., et al., *Determinants of costs of care for patients with Alzheimer's disease*. Int J Geriatr Psychiatry, 2006. 21(5): p. 449-59.
4. Lowin, A., M. Knapp, and P. McCrone, *Alzheimer's disease in the UK: comparative evidence on cost of illness and volume of health services research funding*. Int J Geriatr Psychiatry, 2001. 16(12): p. 1143-8.
5. Fillit, H., J. W. Hill, and R. Futterman, *Health care utilization and costs of Alzheimer's disease: the role of co-morbid conditions, disease stage, and pharmacotherapy*. Fam Med, 2002. 34(7): p. 528-35.
6. Evans, D. A., *Estimated prevalence of Alzheimer's disease in the United States*. Milbank Q, 1990. 68(2): p. 267-89.
7. Hy, L. X. and D. M. Keller, *Prevalence of AD among whites: a summary by levels of severity*. Neurology, 2000. 55(2): p. 198-204.
8. Jorm, A. F. and D. Jolley, *The incidence of dementia: a meta-analysis*. Neurology, 1998. 51(3): p. 728-33.
9. Brookmeyer, R., et al., *Forecasting the global burden of Alzheimer's disease*. Alzheimer's & Dementia, 2007. 3(3): p. 186-191.
10. Kennedy, G. J., et al., *Amyloid-Based interventions in Alzheimer's disease*. CNS Spectr, 2007. 12(12 Suppl 1): p. 1-14.
11. Petersen, R. C., et al., *Mild cognitive impairment: clinical characterization and outcome [published erratum appears in arch neurol 1999 jun; 56(6): 760].: Evidence for activation of microglia in patients with psychiatric illnesses*. Archives of Neurology: Neuroscience Letters, 1999 March 1999 Aug. 20. 56. 271(3. 2): p. 303-8-126-8.
12. Dubois, B., et al., *Research criteria for the diagnosis of Alzheimer's disease: revising the NINCDS-ADRDA criteria*. Lancet Neurol, 2007. 6(8): p. 734-46.
13. Petersen, R. C., et al., *Practice parameter: early detection of dementia: mild cognitive impairment (an evidence-based review). Report of the Quality Standards Subcom-* mittee of the American Academy of Neurology. Neurology, 2001. 56(9): p. 1133-42.
14. Selkoe, D. J., *Toward a comprehensive theory for Alzheimer's disease. Hypothesis: Alzheimer's disease is caused by the cerebral accumulation and cytotoxicity of amyloid beta-protein*. Ann N Y Acad Sci, 2000. 924: p. 17-25.
15. Findeis, M. A., *The role of amyloid beta peptide 42 in Alzheimer's disease*. Pharmacol Ther, 2007.
16. Braak, H. and E. Braak, *Neuropathological staging of Alzheimer-related changes*. Acta Neuropathol, 1991. 82: p. 239-259.
17. Braak, H. and E. Braak, *Evolution of the neuropathology of Alzheimer's disease*. Acta Neurol Scand Suppl, 1996. 165: p. 3-12.
18. Fagan, A. M., et al., *Inverse relation between in vivo amyloid imaging load and cerebrospinal fluid Abeta42 in humans*. Ann Neurol, 2006. 59(3): p. 512-9.
19. Rank, K. B., et al., *Direct interaction of soluble human recombinant tau protein with Abeta 1-42 results in tau aggregation and hyperphosphorylation by tau protein kinase II*. FEBS Lett, 2002. 514(2-3): p. 263-8.
20. King, M. E., et al., *Tau-dependent microtubule disassembly initiated by prefibrillar beta-amyloid*. J Cell Biol, 2006. 175(4): p. 541-6.
21. Chai, C. K., *The genetics of Alzheimer's disease*. Am J Alzheimers Dis Other Demen, 2007. 22(1): p. 37-41.
22. Selkoe, D. J., *Alzheimer's disease: genotypes, phenotypes and treatments*. Science, 1997. 275PBS Record: 790: p. 630-631.
23. Snowdon, D. A., et al., *Brain infarction and the clinical expression of Alzheimer disease. The Nun Study*. Jama, 1997. 277(10): p. 813-7.
24. Cirrito, J. R., et al., *In vivo assessment of brain interstitial fluid with microdialysis reveals plaque-associated changes in amyloid-beta metabolism and half-life*. J Neurosci, 2003. 23(26): p. 8844-53.
25. Monsonego, A., et al., *Immune hyporesponsiveness to amyloid beta peptide in amyloid precursor protein transgenic mice: implications for the pathogenesis and treatment of Alzheimer's disease*. Proc Natl Acad Sci USA, 2001. 98(18): p. 10273-8.
26. Shoji, M., et al., *The levels of cerebrospinal fluid Abeta40 and Abeta42(43) are regulated age-dependently*. Neurobiol Aging, 2001. 22(2): p. 209-15.
27. Andreasen, N., et al., *Cerebrospinal fluid levels of total-tau, phospho-tau and Abeta 42 predicts development of Alzheimer's disease in patients with mild cognitive impairment*. Acta Neurol Scand Suppl, 2003. 179: p. 47-51.
28. Hansson, O., et al., *Association between CSF biomarkers and incipient Alzheimer's disease in patients with mild cognitive impairment: a follow-up study*. Lancet Neurol, 2006. 5(3): p. 228-34.
29. Strozyk, D., et al., *CSF Abeta 42 levels correlate with amyloid-neuropathology in a population-based autopsy study*. Neurology, 2003. 60(4): p. 652-6.
30. Braak, H. and E. Braak, *Frequency of stages of Alzheimer-related lesions in different age categories*. Neurobiol Aging, 1997. 18(4): p. 351-7.
31. Gauthier, S., et al., *Mild cognitive impairment*. Lancet, 2006. 367(9518): p. 1262-70.
32. Small, G. W., et al., *PET of brain amyloid and tau in mild cognitive impairment*. N Engl J Med, 2006. 355(25): p. 2652-63.
33. Price, J. C., et al., *Kinetic modeling of amyloid binding in humans using PET imaging and Pittsburgh Compound-B*. J Cereb Blood Flow Metab, 2005. 25(11): p. 1528-47.
34. Kemppainen, N. M., et al., *PET amyloid ligand [11C] PIB uptake is increased in mild cognitive impairment*. Neurology, 2007. 68(19): p. 1603-6.
35. Vellas, B., et al., *Disease-modifying trials in Alzheimer's disease: a European task force consensus*. Lancet Neurol, 2007. 6(1): p. 56-62.
36. Schenk, D., et al., *Immunization with amyloid-beta attenuates Alzheimer-disease-like pathology in the PDAPP mouse*. Nature, 1999. 400(6740): p. 173-7.
37. Schenk, D., *Amyloid-beta immunotherapy for Alzheimer's disease: the end of the beginning*. Nat Rev Neurosci, 2002. 3(10): p. 824-8.
38. Simard, A. R., et al., *Bone marrow-derived microglia play a critical role in restricting senile plaque formation in Alzheimer's disease*. Neuron, 2006. 49(4): p. 489-502.
39. Fiala, M., et al., *Ineffective phagocytosis of amyloid-beta by macrophages of Alzheimer's disease patients*. J Alzheimers Dis, 2005. 7(3): p. 221-32; discussion 255-62.
40. Haynes, S. E., et al., *The P2Y12 receptor regulates microglial activation by extracellular nucleotides*. Nat Neurosci, 2006. 9(12): p. 1512-9.
41. El Khoury, J., et al., *Ccr2 deficiency impairs microglial accumulation and accelerates progression of Alzheimer-like disease*. Nat Med, 2007. 13(4): p. 432-8.
42. Koizumi, S., et al., *UDP acting at P2Y6 receptors is a mediator of microglial phagocytosis*. Nature, 2007. 446 (7139): p. 1091-5.
43. Wang, R., et al., *The profile of soluble amyloid beta protein in cultured cell media. Detection and quantification of amyloid beta protein and variants by immunoprecipitation-mass spectrometry*. J Biol Chem, 1996. 271 (50): p. 31894-902.
44. Portelius, E., et al., *An Alzheimer's disease-specific beta-amyloid fragment signature in cerebrospinal fluid*. Neurosci Lett, 2006. 409(3): p. 215-9.

The invention claimed is:

1. A method of detecting differential levels of fragments of phagocytosed Aβ peptide in a sample obtained from a patient comprising the steps of:
   (i) subjecting a sample selected from a cerebro-spinal fluid sample and a blood sample obtained from the patient to cell sorting to isolate activated macrophages that display CD14 and CD16 cell surface markers;
   (ii) lysing said activated macrophages and immunoprecipitating any Aβ peptide fragments obtained from said lysed activated macrophages, wherein said Aβ peptide fragments result from intracellular degradation of phagocytosed Aβ peptide proteins; and
   (iii) detecting the level of said Aβ peptide fragments immunoprecipitated from said activated macrophages.

2. A method according to claim 1, wherein said activated macrophages obtained from the patient are sorted by a technique selected from fluorescence activated cell sorting and magnetic extraction.

3. A method according to claim 1, wherein in step (iii), the level of said Aβ peptide fragments is detected by a technique selected from the group consisting of HPLC-fluorescence, HPLC-UV, luminescence and streptavidin/biotin systems.

4. A method according to claim 1, further comprising the step of detecting the level of at least one additional protein marker of Alzheimer's Disease selected from the group consisting of Aβ42, Tau, Phospho-Tau, Aβ42/Aβ40 ratio, or combinations thereof, wherein the presence of said additional protein marker and/or the presence of abnormal levels of the protein marker fragments in the macrophages is indicative of the presence of Alzheimer's Disease in the patient.

5. A method according to claim 1, wherein step (iii) is conducted with an antibody or fragment thereof that specifically binds Aβ peptide and an antibody or fragment thereof that specifically binds a macrophage.

6. A method according to claim 1, wherein the cerebro-spinal fluid sample is obtained from the patient by lumbar puncture.

7. The method of claim 1, wherein step (iii) is conducted with an antibody that specifically binds to a fragment of the Aβ peptide.

8. The method of claim 1, wherein step (iii) is conducted with an antibody that specifically binds to Aβ peptide.

9. A method according to claim 1, further comprising identifying the patient as having Alzheimer's Disease when the detected level of said Aβ peptide fragments is reduced as compared to the standard level.

* * * * *